(12) United States Patent
Bresnick et al.

(10) Patent No.: US 11,053,475 B2
(45) Date of Patent: Jul. 6, 2021

(54) METHODS OF EXPANDING HEMATOPOIETIC STEM CELLS, COMPOSITIONS, AND METHODS OF USE THEREOF

(71) Applicant: WISCONSIN ALUMNI RESEARCH FOUNDATION, Madison, WI (US)

(72) Inventors: Emery H. Bresnick, Middleton, WI (US); Xin Gao, Madison, WI (US); Kirby D. Johnson, Middleton, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 0 days.

(21) Appl. No.: 16/749,190

(22) Filed: Jan. 22, 2020

(65) Prior Publication Data
US 2020/0149011 A1    May 14, 2020

Related U.S. Application Data

(62) Division of application No. 15/758,396, filed as application No. PCT/US2016/053278 on Sep. 23, 2016, now Pat. No. 10,584,315.
(Continued)

(51) Int. Cl.
*A61K 48/00* (2006.01)
*C12N 15/11* (2006.01)
(Continued)

(52) U.S. Cl.
CPC ........ *C12N 5/0647* (2013.01); *C12N 15/1138* (2013.01); *C12N 2310/14* (2013.01); *C12N 2310/531* (2013.01); *C12N 2501/60* (2013.01)

(58) Field of Classification Search
CPC .. A61K 8/68; C12N 2310/14; C12N 15/1138; C12N 5/0647
See application file for complete search history.

(56) References Cited

U.S. PATENT DOCUMENTS

| 5,093,246 A | 3/1992 | Cech et al. |
| 5,633,133 A | 5/1997 | Long et al. |

(Continued)

FOREIGN PATENT DOCUMENTS

| WO | 198804300 | 6/1988 |
| WO | 2004045543 A2 | 6/2004 |

(Continued)

OTHER PUBLICATIONS

Hongbo Xu et al.; "Identification of GPR65, a Novel Regulator of Matrix Metalloproteinases Using High Through-put Screening"; Biochemical and Biophysical Research Communications; 436; pp. 96-103; (2013).

(Continued)

*Primary Examiner* — Terra C Gibbs
(74) *Attorney, Agent, or Firm* — Cantor Colburn LLP

(57) ABSTRACT

Described herein are methods of expanding a population of hematopoietic stem cells by contacting the population of hematopoietic stem cells with an effective amount of an inhibitor of G-protein coupled receptor 65 (GPR65) and providing a population of expanded, substantially undifferentiated hematopoietic stem cells. Exemplary GPR65 inhibitors include siRNAs and certain sphingolipids. Also described are populations of expanded hematopoietic stem cells produced by the methods, media and kits containing GPR65 inhibitors, and methods for administering an expanded population of hematopoietic stem cells to patients.

17 Claims, 28 Drawing Sheets
Specification includes a Sequence Listing.

Related U.S. Application Data

(60) Provisional application No. 62/222,921, filed on Sep. 24, 2015.

(51) Int. Cl.
*C07H 21/02* (2006.01)
*C07H 21/04* (2006.01)
*C12N 5/0789* (2010.01)
*C12N 15/113* (2010.01)

(56) References Cited

U.S. PATENT DOCUMENTS

| | | |
|---|---|---|
| 6,251,588 B1 | 6/2001 | Shannon et al. |
| 2005/0223427 A1 | 10/2005 | Leake et al. |
| 2005/0255487 A1 | 11/2005 | Khvorova et al. |
| 2015/0004145 A1 | 1/2015 | Lemischka et al. |
| 2018/0245045 A1 | 8/2018 | Bresnick et al. |

FOREIGN PATENT DOCUMENTS

| | | |
|---|---|---|
| WO | 2004090105 A2 | 10/2004 |
| WO | 2005078094 A2 | 8/2005 |
| WO | 2008101354 A1 | 8/2008 |
| WO | 2010017551 A2 | 2/2010 |

OTHER PUBLICATIONS

International Search Report and Written Opinion; International Application No. PCT/US2016/053278; International Filing Date Sep. 23, 2016; dated Dec. 20, 2016; 15 pages.

ISR/WO, issued Dec. 20, 2016.

Kartalaei et al.; "Whole-transcriptome Analysis of Endothelial to Hematopoietic Stem Cell Transition Reveals a Requirement for Gpr56 in HSC Generation"; Journal of Experimental Medicine; 212(1); pp. 93-S3; (2015).

Saito et al.; Maintenance of the Hematopoietic Stem Cell Pool in Bone Marrow Niches by EVI1-regulated GPR56; Leukemia; 27; pp. 1637-1649; (2013).

Schueler et al.; "Toxicity of Glucosylsphingosine (glucopsychosine) to Cultured Neuronal Cells: a Model System for Assessing Neuronal Damage in Gaucher Disease Type 2 and 3"; Neurobiology of Disease; 14; pp. 595-601; (2003).

Xin Gao et al.; "GATA Factor-G-Protein-Coupled Receptor Circuit Suppresses Hematopoiesis"; Stem Cell Reports; 6(3); pp. 368-382; (2016).

METHODS OF EXPANDING HEMATOPOIETIC STEM CELLS, COMPOSITIONS, AND METHODS OF USE THEREOF

CROSS REFERENCE TO RELATED APPLICATIONS

This application is divisional of U.S. application Ser. No. 15/758,396, filed on Mar. 8, 2018, which is a National Stage application of PCT/US2016/053278, filed Sep. 23, 2016, which claims the benefit of U.S. Provisional Application No. 62/222,921, filed Sep. 24, 2015, both of which are incorporated by reference in their entirety herein.

STATEMENT REGARDING FEDERALLY SPONSORED RESEARCH & DEVELOPMENT

This invention was made with government support under DK068634 awarded by the National Institutes of Health. The government has certain rights in the invention.

FIELD OF THE DISCLOSURE

The present disclosure is related to methods of stimulating and/or expanding hematopoietic stem cells by inhibiting suppressors of hematopoietic stem cells.

BACKGROUND

Bone marrow stem cells have been used to treat a variety of diseases including leukemia, multiple myeloma, some types of lymphoma, graft versus host disease, and genetic disorders of the blood and immune system including aplastic anemia, sickle cell anemia, Severe Combined Immune Deficiency (SCID), Wiskott-Aldrich Syndrome (WAS), IPEX Syndrome, Hemophagocytic Lymphohistiocytosis (HLH), X-linked Lymphoproliferative Disease (XLP) and Chronic Granulomatous Disease (CGD). However, it is difficult and time-consuming to find a matching donor for a particular patient. Only a fraction of patients will find a suitable donor, and many patients die due to being unable to find a proper donor. In addition, finding a proper match is especially problematic for African-Americans, Hispanics, Native Americans and people of mixed ethnicity.

Hematopoietic stem cells (HSCs) are rare adult stem cells that have been identified in fetal bone marrow, fetal liver, aorta-gonad-mesonephros (AGM), umbilical cord blood (UCB), adult bone marrow, and peripheral blood, which are capable of differentiating into three cell lineages including myeloerythroid (red blood cells, granulocytes, monocytes), megakaryocyte (platelets) and lymphoid (T-cells, B-cells, and natural killer) cells. HSCs, like bone marrow stem cells, are used in clinical transplantation protocols to treat a variety of diseases including malignant and non-malignant disorders.

Sources of HSCs include bone marrow and peripheral blood. To obtain marrow cells, donors must undergo multiple aspirations to collect several thousand milliliters of bone marrow, a procedure that is carried out under general anesthesia. To collect HSCs from the peripheral blood, the donor must be treated with granulocyte colony-stimulating factor to increase the number of circulating HSCs. Both of these procedures entail some risk and significant cost. Another source of HSCs is umbilical cord blood (UCB). UCB has major advantages over other sources of HSCs, such as that from bone marrow and mobilized peripheral blood. Not only is UCB readily available from many of the nearly 50 UCB banks across the United States, it also shows increased tolerance for mismatches with the host major histocompatability complex (MHC). In addition to relative widespread availability, these HSCs have several useful properties, including their decreased ability to induce immunological reactivity. In many cases, use of UCB incurs significantly less graft-versus-host disease compared to other sources of HSCs.

One barrier to the use of UCB is limited HSC numbers per cord at harvest. As cell dose has been shown to be a major determinant of engraftment and survival after UCB transplantation, low stem cell numbers represents the most significant barrier to successful UCB stem cell transplantation. The ability to expand ex vivo, prior to transplantation, the stem cell components of a single cord blood unit will greatly increase the viability of this treatment modality. Infusing patients with larger numbers of stem cells as opposed the limited cells available in an unexpanded cord blood unit, should greatly increase the likelihood of successful engraftment.

Expansion of HSCs has remained an important goal to develop advanced cell therapies for bone marrow transplantation and many blood disorders. Despite the identification of several hematopoietic growth factors, only limited expansion of HSCs has been observed. There thus remains a need for new methods of expanding HSCs, particularly ex vivo methods.

BRIEF SUMMARY

In one aspect, a method of expanding a population of hematopoietic stem cells comprises contacting the population of hematopoietic stem cells with an effective amount of an inhibitor of G-protein coupled receptor 65 (GPR65) and providing a population of expanded, substantially undifferentiated hematopoietic stem cells. Also included is an expanded, substantially undifferentiated HSC population made by the foregoing process.

In another embodiment, a kit for expanding, ex vivo, the number of hematopoietic stem cells in a population of hematopoietic stem cells comprises an inhibitor of G-protein coupled receptor 65 (GPR65), and instructions for the use of the inhibitor of G-protein coupled receptor 65 (GPR65), wherein, when used, the kit provides expanded number of hematopoietic stem cells.

In another aspect, a medium for carrying out ex vivo expansion of hematopoietic stem cells in a population of hematopoietic stem cells comprises a fluid medium suitable for maintaining viable stem cells, and an inhibitor of G-protein coupled receptor 65 (GPR65) present in the medium at a concentration suitable to provide expansion of the population of HSCs.

In a still further aspect, a method for administering an expanded population of hematopoietic stem cells to a patient in need thereof, comprises culturing a population of hematopoietic stem cells ex vivo in a hematopoietic stem cell expansion medium for a period of time sufficient to provide an expanded population of hematopoietic stem cells, wherein the hematopoietic stem cell expansion media comprises an inhibitor of G-protein coupled receptor 65 (GPR65), and administering the expanded population of hematopoietic stem cells to the patient.

Figure 1A:
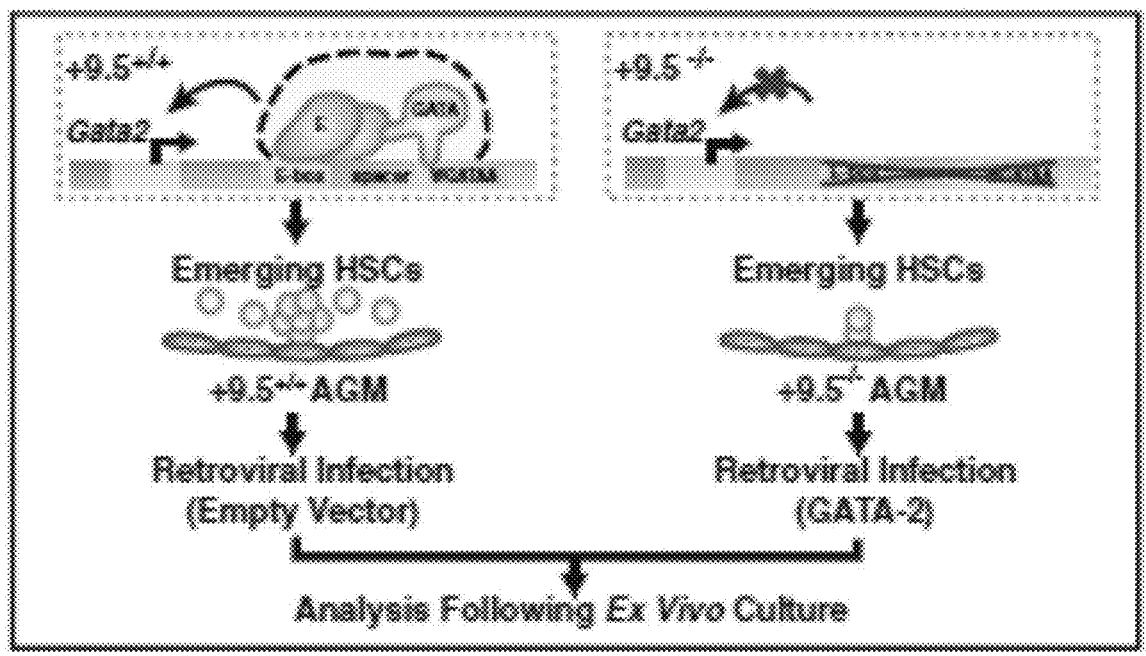
FIGS. 1 A-F show GATA-2 expression in +9.5$^{-/-}$ AGM rescues CD31$^+$c-KIT$^+$ hematopoietic and CD31$^+$c-KIT$^-$ endothelial cells. (A) AGM ex vivo retroviral infection and culture. (B) Flow cytometric analysis of GFP$^+$ cells within total live cells (6 litters: +9.5$^{+/+}$-Empty [n=8 embryos]; +9.5$^{-/-}$-Empty [n=4 embryos]; +9.5$^{-/-}$-GATA-2 [n=6 embryos]). (C) RT-PCR analysis of Gata2 mRNA levels in FACS-sorted CD31$^+$c-KIT$^-$ and CD31$^+$c-KIT$^+$ cells (6 litters: +9.5$^{+/+}$-Empty [n=8 embryos]; +9.5$^{-/-}$-Empty [n=4 embryos]; +9.5$^{-/-}$-GATA-2 [n=6 embryos]). (D) Representative plots from flow cytometric analysis of CD31$^+$c-KIT$^+$ and CD31$^+$c-KIT$^-$ cell populations in infected AGMs after 96 h of ex vivo culture. (E and F) Quantitation of flow cytometry data expressed as the percentage of CD31$^+$c-KIT$^-$ and CD31$^+$c-KIT$^+$ cells in GPF$^+$ cells (E) and the percentage of GFP$^+$ cells in CD31$^+$c-KIT$^-$ and CD31$^+$c-KIT$^+$ cells (F) (6 litters: +9.5$^{+/+}$-Empty [n=8 embryos]; +9.5$^{-/-}$-Empty [n=4 embryos]; +9.5$^{-/-}$-GATA-2 [n=6 embryos]). Error bars represent SEM. *, P<0.05;, P<0.01; *, P<0.001 (two-tailed unpaired Student's t-test).

The above-described and other features will be appreciated and understood by those skilled in the art from the following detailed description, drawings, and appended claims.

DETAILED DESCRIPTION

Described herein are novel methods of expanding hematopoietic stem cells (HSCs). The inventors of the present application have unexpectedly found that GATA-2, a positive regulator of hematopoiesis, upregulated Gpr65, which encodes a negative regulator of hematopoiesis. Thus, inhibitors of G-protein coupled receptor 65 (GPR65) can be used to provide populations of expanded, substantially undifferentiated hematopoietic stem cells. Such expanded hematopoietic stem cell populations are critical for the development of advanced cell therapies for bone marrow transplantation and many blood disorders.

Establishment and maintenance of the adult hematopoietic system requires HSCs generated from a unique type of endothelial cell (hemogenic) in the aorta-gonad-mesonephros (AGM) region of the mammalian embryo. HSCs develop in cell clusters that bud off from hemogenic endothelium, a process termed endothelial to hematopoietic transition (EHT). The HSCs migrate to and colonize the fetal liver and subsequently the bone marrow.

Many questions remain unanswered regarding the molecular constituents and mechanistic steps controlling EHT. Considerable efforts have focused on defining the relevant regulatory proteins and networks. An emerging theme is that master regulatory transcription factors co-localize at cis-elements of target genes and establish complex genetic networks that control hematopoiesis. Whether this combinatorial mechanism operates in hemogenic endothelium is unclear, and the relationship between mechanisms controlling EHT and those conferring HSC multipotency is not understood. A shared component of the mechanisms involves the transcription factor GATA-2, which is essential for definitive hematopoiesis. GATA-2 functions in hemogenic endothelium to induce EHT and promotes HSC function.

Evidence for GATA-2 control of EHT emerged from analysis of mutant mice lacking a Gata2 intronic cis-regulatory element (+9.5) and from conditional Gata2 knockout mice. GATA-2 occupies sites −77, −3.9, −2.8, −1.8 upstream and an intronic site +9.5 kb downstream of the Gata2 1S promoter, and GATA-1 replacement of GATA-2 at these sites is tightly linked to Gata2 repression during erythropoiesis. Unlike deletions of the other GATA-2 occupancy sites, the +9.5 site deletion uniquely decreases Gata2 expression in AGM hemogenic endothelium, deregulates genes encoding positive regulators of hematopoiesis, and abrogates hemogenic endothelial activity to generate HSCs. The defective HSC generator of +9.5$^{-/-}$ embryos causes a severe HSPC deficiency in the fetal liver and embryonic lethality at E13-14.

GATA-2 regulates a large gene cohort in hemogenic endothelium, and the individual gene constituents do not parse into a predominant molecular pathway. These constituents include Runx1, Lyl1, and Mp1, positive mediators of HSC generation and/or function. The identification of constituents of the GATA-2-dependent genetic network bearing these attributes will reveal how GATA-2 triggers endothelium to form a stem cell. Moreover, as GATA-2 lacks ligand binding and catalytic sites, features that can be leveraged for small molecule/drug binding, these mechanistic insights will usher in strategies to promote HSC generation/function for transplantation and to inhibit proliferation or survival of HSPC-derived leukemia cells.

The most common targets for FDA-approved drugs are the GPCRs. The GPCR family consists of 341 non-olfactory receptors that are classified as rhodopsin, secretin, glutamate, adhesion and Frizzed/Taste2 based on sequence homology. CXCR4, a rhodopsin-like GPCR, has a critical role in HSPC survival, proliferation, migration and engraftment. CXCR4 antagonists are used as mobilizing agents for stem cell transplantation. Previously, the present inventors described +9.5 site-mediated upregulation of Gpr56 expression, and a loss-of-function analysis indicated that GPR56 promotes HSC emergence in the AGM. However, analyses of the role of Gpr56 in HSC maintenance and function yielded opposite conclusions—either it had no role or it promoted HSC maintenance.

By systematically profiling expression of the entire GPCR cohort in the AGM, the present inventors have now discovered a small subset of GATA-2-regulated GPCRs, a smaller cohort that are GATA-2- and GATA-1-regulated, and one in particular, GPR65, that suppresses AGM hematopoiesis. Surprisingly, GATA-2, a positive regulator of hematopoiesis, upregulated Gpr65, which encodes a negative regulator of hematopoiesis. These results provide evidence for a GATA factor-GPCR incoherent type I feedforward loop as a vital component of the GATA-2-dependent genetic network that controls HSC emergence.

In one aspect, a method of expanding a population of hematopoietic stem cells comprises contacting the population of hematopoietic stem cells with an effective amount of an inhibitor of G-protein coupled receptor 65 (GPR65) and providing a population of expanded, substantially undifferentiated hematopoietic stem cells. For example, the method comprises culturing the population of HSCs in an HSC expansion medium for a period of time sufficient to expand the number of HSCs in the HSC population, wherein the HSC expansion media comprises an inhibitor of G-protein coupled receptor 65 (GPR65).

As used herein, "expand", "expanding" and like terms means to increase the number of undifferentiated HSCs in the population relative to the number of HSCs in the original population in vitro, in vivo or ex vivo using any of the methods disclosed herein. The expansion of the HSCs can be evaluated by a cell marker analysis (for example, counting the cells corresponding to $CD34^+$ by FACS), quantitative analysis based on the colony assay method, and the like. In one aspect, expanding is ex vivo and the number of undifferentiated cells in the population of HSCs is increased by greater than 1.25-fold. In one aspect, the population of HSCs is enriched to a clinically relevant number. In one aspect, the population of HSCs is enriched for $CD34^+$ cells, meaning that the percentage of $CD34^+$ cells relative to other cells in a population is increased. Additional stem cell markers include $CD38^-$, $DR^-$, $CD45^+$, $CD90^+$, $CD117^+$, $CD123^+$, and $CD133^+$.

In certain aspect, the expanded HSC population has "long term, multi-lineage repopulating potential" meaning that the expanded HSCs are capable of repopulating many different types of blood cells in irradiated recipients upon transplantation and/or cells that possess high proliferative potential in vitro.

An HSC population is "substantially undifferentiated" if a sufficient number of cells in that population retain the ability to self-renew and can give rise to various differentiated cell types when transplanted into a recipient, for example, in the case of an HSC population, repopulating the HSC lineage when transplanted. As used herein, "without significant differentiation" means the expanded stem cell population has a sufficient number of cells that maintain a multi-lineage differentiation potential that the full scope of a target stem lineage may be regenerated upon transplantation of the expanded stem cell population into a recipient. For example, the expanded HSC population, when transplanted into a recipient, is capable of regenerating the entire hematopoietic cell lineage.

In an embodiment, the population of HSCs is obtained from a mammalian tissue selected from umbilical cord blood, peripheral blood, and bone marrow. HSCs may be the subject's own cells (autologous) or those of a donor (allogeneic). In a more specific embodiment, the population of HSCs is obtained from mammalian cord blood. In certain aspects, the HSCs are of human origin.

As used herein, "obtained" from a tissue means a conventional method of harvesting or partitioning tissue from a donor. For example, the tissue may be obtained from a blood sample, such as a peripheral or cord blood sample, or harvested from bone marrow. Methods for obtaining such samples are well known to one of ordinary skill in the art. The samples may be fresh, i.e., obtained from the donor without freezing. Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Donor animals are mammals including a primate, such as a human; or laboratory animals such as mice, rats, dogs, and pigs. The sample may be obtained from an autologous or allogeneic donor or source. In certain aspects, the sample is obtained from an autologous source. Methods for isolation of hematopoietic stem cells may involve subsequent purification techniques based on cell surface markers and functional characteristics.

In another aspect, included herein is an expanded, substantially undifferentiated HSC population made by contacting a population of hematopoietic stem cells with an effective amount of an inhibitor of G-protein coupled receptor 65 (GPR65) to provide the population of expanded, substantially undifferentiated hematopoietic stem cells.

Further included herein is a kit for expanding, ex vivo, the number of hematopoietic stem cells (HSC) in a population of HSCs, the kit comprising an inhibitor of G-protein coupled receptor 65 (GPR65), and instructions for the use of the inhibitor of G-protein coupled receptor 65 (GPR65), wherein, when used, the kit provides expanded number of HSCs. Exemplary instructions for use include, for example, a detailed description of the kit components, reaction times/temperature for expanding HSCs, and the like.

In another aspect, a medium for carrying out ex vivo expansion of HSCs in a population of HSCs comprises a fluid medium suitable for maintaining viable stem cells, and an inhibitor of G-protein coupled receptor 65 (GPR65) present in the medium at a concentration suitable to provide expansion of the population of HSCs. An "HSC expansion medium" is a medium suitable for expanding the number of HSCs in a culture and includes, for example, StemPro® 34 medium, GE HyClone® medium, Stemline® HSC expansion medium from Sigma-Aldrich, and StemSpan™ SFEM II from STEMCELL Technologies. The medium comprises e.g., 20 μm of an inhibitor of G-protein coupled receptor 65 (GPR65) for example.

A further embodiment includes a method for administering an expanded population of hematopoietic stem cells to a patient in need thereof, comprising culturing a population of hematopoietic stem cells ex vivo in a hematopoietic stem cell expansion medium for a period of time sufficient to provide an expanded population of hematopoietic stem cells, wherein the hematopoietic stem cell expansion medium comprises an inhibitor of G-protein coupled receptor 65 (GPR65), and administering the expanded population of hematopoietic stem cells to the patient. Exemplary patients include patients in need of treatment for leukemia, multiple myeloma, some types of lymphoma, graft versus host disease, and genetic disorders of the blood and immune system including aplastic anemia, sickle cell anemia, Severe Combined Immune Deficiency (SCID), Wiskott-Aldrich Syndrome (WAS), IPEX Syndrome, Hemophagocytic Lymphohistiocytosis (HLH), X-linked Lymphoproliferative Disease (XLP) and Chronic Granulomatous Disease (CGD).

In one aspect, the method provides expanded HSCs that, upon transplant into a recipient, exhibit greater than 5% donor repopulation, such as greater than 10%, 15%, 20%, 25%, 30%, 35%, 40%, 55%, 60%, 65%, 70%, 75%, 80%, 85%, or 90% donor repopulation. Specifically, the method provides expanded HSCs that, upon transplant into a recipient, exhibit greater than 25%, 35%, 45%, or 60% donor repopulation. An exemplary recipient is a mammal, for example, a primate, such as a human; or laboratory animals such as mice, rats, dogs, and pigs. The term "recipient" is used interchangeably with "patient."

In one aspect, the inhibitor of G-protein coupled receptor 65 (GPR65) is a glucosphingolipid or a galactosphingolipid as well as their salts and derivatives. Exemplary compounds include psychosine (galactosphingolipid), dihydropsychosine, lysosulfatide (sulfogalactosylsphingosine), and glucosylsphingosine, and the like.

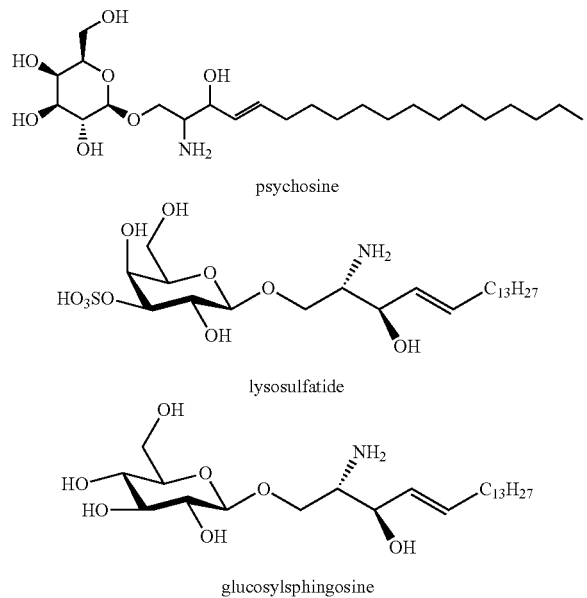

In another aspect, the inhibitor of G-protein coupled receptor 65 (GPR65) is an antibody that both binds to and inhibits G-protein coupled receptor 65 (GPR65).

In one aspect, the GPR65 inhibitor is an inhibitory nucleic acid molecule, wherein administration of the inhibitory nucleic acid molecule selectively decreases the expression of GPR65. The term "inhibitory nucleic acid molecule" means a single stranded, double-stranded or triple-stranded RNA or DNA, specifically RNA, such as triplex oligonucleotides, ribozymes, aptamers, small interfering RNA including siRNA (short interfering RNA) and shRNA (short hairpin RNA), antisense RNA, or a portion thereof, or an analog or mimetic thereof, that is capable of reducing or inhibiting the expression of a target gene or sequence. Inhibitory nucleic acids can act by, for example, mediating the degradation or inhibiting the translation of mRNAs which are complementary to the interfering RNA sequence. An inhibitory nucleic acid, when administered to a mammalian cell, results in a decrease (e.g., by 5%, 10%, 25%, 50%, 75%, or even 90-100%) in the expression (e.g., transcription or translation) of a target sequence. Typically, a nucleic acid inhibitor comprises or corresponds to at least a portion of a target nucleic acid molecule, or an ortholog thereof, or comprises at least a portion of the complementary strand of a target nucleic acid molecule. Inhibitory nucleic acids may have substantial or complete identity to the target gene or sequence, or may include a region of mismatch (i.e., a mismatch motif). The sequence of the inhibitory nucleic acid can correspond to the full-length target gene, or a subsequence thereof. In one aspect, the inhibitory nucleic acid molecules are chemically synthesized.

The specific sequence utilized in design of the inhibitory nucleic acids is a contiguous sequence of nucleotides contained within the expressed gene message of the target. Factors that govern a target site for the inhibitory nucleic acid sequence include the length of the nucleic acid, binding affinity, and accessibility of the target sequence. Sequences may be screened in vitro for potency of their inhibitory activity by measuring inhibition of target protein translation and target related phenotype, e.g., inhibition of cell proliferation in cells in culture. In general it is known that most regions of the RNA (5' and 3' untranslated regions, AUG initiation, coding, splice junctions and introns) can be targeted using antisense oligonucleotides. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Phosphorothioate antisense oligonucleotides may be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. A peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Short interfering (si) RNA technology (also known as RNAi) generally involves degradation of an mRNA of a particular sequence induced by double-stranded RNA (dsRNA) that is homologous to that sequence, thereby "interfering" with expression of the corresponding gene. A selected gene may be repressed by introducing a dsRNA which corresponds to all or a substantial part of the mRNA for that gene. Without being held to theory, it is believed that when a long dsRNA is expressed, it is initially processed by a ribonuclease III into shorter dsRNA oligonucleotides of as few as 21 to 22 base pairs in length. Accordingly, siRNA may be effected by introduction or expression of relatively short homologous dsRNAs. Exemplary siRNAs have sense and antisense strands of about 21 nucleotides that form approximately 19 nucleotides of double stranded RNA with overhangs of two nucleotides at each 3' end.

siRNA has proven to be an effective means of decreasing gene expression in a variety of cell types. siRNA typically decreases expression of a gene to lower levels than that achieved using antisense techniques, and frequently eliminates expression entirely. In mammalian cells, siRNAs are effective at concentrations that are several orders of magnitude below the concentrations typically used in antisense experiments.

The double stranded oligonucleotides used to effect RNAi are specifically less than 30 base pairs in length, for example, about 29, 28, 27, 26, 25, 24, 23, 22, 21, 20, 19, 18, or 17 base pairs or less in length, and contain a segment sufficiently complementary to the target mRNA to allow hybridization to the target mRNA. Optionally, the dsRNA oligonucleotide includes 3' overhang ends. Exemplary 2-nucleotide 3' overhangs are composed of ribonucleotide residues of any type and may be composed of 2'-deoxythymidine residues, which lowers the cost of RNA synthesis and may enhance nuclease resistance of siRNAs in the cell culture medium and within transfected cells. Exemplary dsRNAs are synthesized chemically or produced in vitro or in vivo using appropriate expression vectors. Longer RNAs may be transcribed from promoters, such as T7 RNA polymerase promoters, known in the art.

Longer dsRNAs of 50, 75, 100, or even 500 base pairs or more also may be utilized in certain embodiments. Exemplary concentrations of dsRNAs for effecting RNAi are about 0.05 nM, 0.1 nM, 0.5 nM, 1.0 nM, 1.5 nM, 25 nM, or 100 nM, although other concentrations may be utilized depending upon the nature of the cells treated, the gene target and other factors readily identified by one of ordinary skill in the art.

Compared to siRNA, shRNA offers advantages in silencing longevity and delivery options. Vectors that produce shRNAs, which are processed intracellularly into short duplex RNAs having siRNA-like properties provide a renewable source of a gene-silencing reagent that can mediate persistent gene silencing after stable integration of the vector into the host-cell genome. Furthermore, the core silencing 'hairpin' cassette can be readily inserted into retroviral, lentiviral, or adenoviral vectors, facilitating delivery of shRNAs into a broad range of cell types.

A hairpin can be organized in either a left-handed hairpin (i.e., 5'-antisense-loop-sense-3') or a right-handed hairpin (i.e., 5'-sense-loop-antisense-3'). The shRNA may also contain overhangs at either the 5' or 3' end of either the sense strand or the antisense strand, depending upon the organization of the hairpin. If there are any overhangs, they are specifically on the 3' end of the hairpin and include 1 to 6 bases. The overhangs can be unmodified, or can contain one or more specificity or stabilizing modifications, such as a halogen or O-alkyl modification of the 2' position, or internucleotide modifications such as phosphorothioate, phosphorodithioate, or methylphosphonate modifications. The overhangs can be ribonucleic acid, deoxyribonucleic acid, or a combination of ribonucleic acid and deoxyribonucleic acid.

Additionally, a hairpin can further comprise a phosphate group on the 5'-most nucleotide. The phosphorylation of the 5'-most nucleotide refers to the presence of one or more phosphate groups attached to the 5' carbon of the sugar moiety of the 5'-terminal nucleotide. Specifically, there is only one phosphate group on the 5' end of the region that will form the antisense strand following Dicer processing. In one exemplary embodiment, a right-handed hairpin can include a 5' end (i.e., the free 5' end of the sense region) that does not have a 5' phosphate group, or can have the 5' carbon of the free 5'-most nucleotide of the sense region being modified in such a way that prevents phosphorylation. This can be achieved by a variety of methods including, but not limited to, addition of a phosphorylation blocking group (e.g., a 5'-O-alkyl group), or elimination of the 5'-OH functional group (e.g., the 5'-most nucleotide is a 5'-deoxy nucleotide). In cases where the hairpin is a left-handed hairpin, preferably the 5' carbon position of the 5'-most nucleotide is phosphorylated.

Hairpins that have stem lengths longer than 26 base pairs can be processed by Dicer such that some portions are not part of the resulting siRNA that facilitates mRNA degradation. Accordingly the first region, which may include sense nucleotides, and the second region, which may include antisense nucleotides, may also contain a stretch of nucleotides that are complementary (or at least substantially complementary to each other), but are or are not the same as or complementary to the target mRNA. While the stem of the shRNA can include complementary or partially complementary antisense and sense strands exclusive of overhangs, the shRNA can also include the following: (1) the portion of the molecule that is distal to the eventual Dicer cut site contains a region that is substantially complementary/homologous to the target mRNA; and (2) the region of the stem that is proximal to the Dicer cut site (i.e., the region adjacent to the loop) is unrelated or only partially related (e.g., complementary/homologous) to the target mRNA. The nucleotide content of this second region can be chosen based on a number of parameters including but not limited to thermodynamic traits or profiles.

Modified shRNAs can retain the modifications in the post-Dicer processed duplex. In exemplary embodiments, in cases in which the hairpin is a right handed hairpin (e.g., 5'-S-loop-AS-3') containing 2-6 nucleotide overhangs on the 3' end of the molecule, 2'-O-methyl modifications can be added to nucleotides at position 2, positions 1 and 2, or positions 1, 2, and 3 at the 5' end of the hairpin. Also, Dicer processing of hairpins with this configuration can retain the 5' end of the sense strand intact, thus preserving the pattern of chemical modification in the post-Dicer processed duplex. Presence of a 3' overhang in this configuration can be particularly advantageous since blunt ended molecules containing the prescribed modification pattern can be further processed by Dicer in such a way that the nucleotides carrying the 2' modifications are removed. In cases where the 3' overhang is present/retained, the resulting duplex carrying the sense-modified nucleotides can have highly favorable traits with respect to silencing specificity and functionality. Examples of exemplary modification patterns are described in detail in U.S. Patent Publication No. 20050223427 and International Patent Publication Nos. WO 2004/090105 and WO 2005/078094, the disclosures of each of which are incorporated by reference herein in their entirety.

shRNA may comprise sequences that were selected at random, or according to a rational design selection procedure. For example, rational design algorithms are described in International Patent Publication No. WO 2004/045543 and U.S. Patent Publication No. 20050255487, the disclosures of which are incorporated herein by reference in their entireties. Additionally, it may be desirable to select sequences in whole or in part based on average internal stability profiles ("AISPs") or regional internal stability profiles ("RISPs") that may facilitate access or processing by cellular machinery.

Ribozymes are enzymatic RNA molecules capable of catalyzing specific cleavage of mRNA, thus preventing translation. The mechanism of ribozyme action involves sequence specific hybridization of the ribozyme molecule to complementary target RNA, followed by an endonucleolytic cleavage event. The ribozyme molecules specifically include (1) one or more sequences complementary to a target mRNA, and (2) the well-known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site-specific recognition sequences can be used to destroy target mRNAs, hammerhead ribozymes may alternatively be used. Hammerhead ribozymes cleave mRNAs at locations dictated by flanking regions that form complementary base pairs with the target mRNA. Specifically, the target mRNA has the following sequence of two bases: 5'-UG-3'. The construction and production of hammerhead ribozymes is well known in the art and is described more fully in U.S. Pat. No. 5,633,133, the contents of which are incorporated herein by reference.

Gene targeting ribozymes may contain a hybridizing region complementary to two regions of a target mRNA, each of which is at least 5, 6, 7, 8, 9, 10, 11, 12, 13, 14, 15, 16, 17, 18, 19, or 20 contiguous nucleotides (but which need not both be the same length).

Hammerhead ribozyme sequences can be embedded in a stable RNA such as a transfer RNA (tRNA) to increase cleavage efficiency in vivo. In particular, RNA polymerase III-mediated expression of tRNA fusion ribozymes is well known in the art. There are typically a number of potential hammerhead ribozyme cleavage sites within a given target cDNA sequence. Specifically, the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the target mRNA would allow the selective targeting of one or the other target genes.

Ribozymes also include RNA endoribonucleases ("Cech-type ribozymes") such as the one which occurs naturally in *Tetrahymena thermophile*, described in International Patent Publication No. WO 88/04300. The Cech-type ribozymes have an eight base pair active site which hybridizes to a target RNA sequence where after cleavage of the target RNA takes place. In one embodiment, Cech-type ribozymes target eight base-pair active site sequences that are present in a target gene or nucleic acid sequence.

Ribozymes can be composed of modified oligonucleotides (e.g., for improved stability, targeting, etc.) and can be chemically synthesized or produced through an expression vector. Because ribozymes, unlike antisense molecules, are catalytic, a lower intracellular concentration is required for efficiency. Additionally, in certain embodiments, a ribozyme may be designed by first identifying a sequence portion sufficient to cause effective knockdown by RNAi. Portions of the same sequence may then be incorporated into a ribozyme.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body. Nucleic acid molecules to be used in triple helix formation for the inhibition of transcription are specifically single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the target sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Inhibitory nucleic acids can be administered directly or delivered to cells by transformation or transfection via a vector, including viral vectors or plasmids, into which has been placed DNA encoding the inhibitory oligonucleotide with the appropriate regulatory sequences, including a promoter, to result in expression of the inhibitory oligonucleotide in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems. In other embodiments, expression may be under the control of tissue or development-specific promoters.

Vectors may be introduced by transfection using carrier compositions such as Lipofectamine 2000 (Life Technologies) or Oligofectamine™ (Life Technologies). Transfection efficiency may be checked using fluorescence microscopy for mammalian cell lines after co-transfection of hGFP-encoding pAD3.

The effectiveness of the inhibitory oligonucleotide may be assessed by any of a number of assays, including reverse transcriptase polymerase chain reaction or Northern blot analysis to determine the level of existing human sclerostin mRNA, or Western blot analysis using antibodies which recognize the human sclerostin protein, after sufficient time for turnover of the endogenous pool after new protein synthesis is repressed.

As used herein, the term substantially complementary means that the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95% identical. Optimal alignment of sequences for comparisons of identity may be conducted using a variety of algorithms known in the art. Sequence identity may also be determined using the BLAST algorithm.

Also included herein is a composition comprising a small interfering RNA, the small interfering RNA comprising 19 to 29 nucleotides that are substantially complementary to a sequence of 19 to 29 nucleotides of Gpr65 (NM_008152; SEQ ID NO: 1). Exemplary small interfering RNAs are siRNA and shRNA.

Further included are pharmaceutical compositions comprising a pharmaceutically acceptable excipient and a small interfering RNA, the small interfering RNA comprising 19 to 29 nucleotides that are substantially complementary to a sequence of 19 to 29 nucleotides of SEQ ID NO: 1. Exemplary shRNAs include:

```
miR-30-context Gpr65 shRNA sequences:
                                      (SEQ ID NO: 2)
TGCTGTTGACAGTGAGCGAGCAGGTTAAGTTACATGGTATTAGTGA

AGCCACAGATGTAATACCATGTAACTTAACCTGCCTGCCTACTGCC

TCGGA (SEQ ID NO: 3)
TGCTGTTGACAGTGAGCGAAAAGATGAAACGAGTGTTGAATAGTGA

AGCCACAGATGTATTCAACACTCGTTTCATCTTTCTGCCTACTGCC

TCGGA
```

In one aspect, the GPR65 inhibitor comprises a small interfering RNA and a glucosphingolipid or a galactosphingolipid.

The invention is further illustrated by the following non-limiting examples.

EXAMPLES

Methods

Mice and embryo generation. Gata2 +9.5$^{+/-}$ mice generated via homologous recombination in ES cells are described in the art. Staged embryos were obtained from timed mating between Gata2 +9.5 heterozygotes. The detection of the vaginal plug was considered as day 0.5. Pregnant females were euthanized with $CO_2$, and fresh embryos were transferred into cold PBS for dissection. Mice and embryos are genotyped by PCR. All animal experiments were carried out with the ethical approval of the AAALAC International (Association for the Assessment and Accreditation of Laboratory Animal Care) at the University of Wisconsin-Madison.

AGM explant culture. AGMs were dissected from E11.5 embryos. Freshly isolated AGMs were infected as below and cultured as described. In brief, intact AGMs were cultured for 4 days on Durapore® filters (Millipore) at the air-liquid interface in IMDM$^+$ Media (Iscove's modified Dulbecco's media [Gibco] supplemented with 20% fetal bovine serum [FBS; Gemini], L-glutamine [Gibco; 4 mM], 1% penicillin/streptomycin [Cellgro], mercaptoethanol [0.1 mM], IL-3 [R&D; 100 ng/ml], Flt3L [R&D; 100 ng/ml], and 1.5% conditioned medium from a Kit ligand-producing CHO cell line).

Primary erythroid precursor cell isolation. Primary erythroid precursors were isolated from E14.5 fetal livers using the EasySep™ negative selection Mouse Hematopoietic Progenitor Cell Enrichment Kit (StemCell Technologies). Briefly, fetal livers were dissociated by pipetting and resuspended at $5\times10^7$ cell/ml in PBS containing 2% FBS, 2.5 mM EDTA, and 10 mM glucose. EasySep™ Mouse Hematopoietic Progenitor Cell Enrichment Cocktail was added at 50 µg/ml supplemented with 2.5 µg/ml biotin-conjugated CD71 antibody (eBioscience). After 15 min incubation on ice, the cells were washed by centrifugation for min at 1200 rpm at 4° C. and resuspended at $5\times10^7$ cell/ml in PBS containing 2% FBS, 2.5 mM EDTA, and 10 mM glucose, and EasySep™ Biotin Selection Cocktail was added at 100 µg/ml. After 15 min incubation at 4° C., EasySep™ Mouse Progenitor Magnetic Microparticles were added at 50 µg/ml. After 10 min incubation at 4° C., cells were resuspended to 2.5 ml and incubated with a magnet for 3 min. Unbound cells were carefully transferred into 15 ml tube and used for subsequent experiments.

Cell culture. G1E-ER-GATA-1 cells were cultured with or without 1 µM estradiol as previously described. Fetal liver erythroid precursor cells were cultured and maintained at a density of $2.5\times10^5-1\times10^6$ cells/ml in StemPro®-34 (Gibco) supplemented with 10% nutrient supplement (Gibco), 2 mM L-glutamine (Cellgro), 1% Penicillin/streptomycin (Cellgro), 100 µM monothioglycerol (Sigma-Aldrich), 1 µM dexamethasone (Sigma-Aldrich), 0.5 U/ml of erythropoietin, and 1% conditioned medium from a kit ligand-producing CHO cell line for expansion. Cells were cultured in a humidified incubator at 37° C. (5% carbon dioxide).

Retroviral infection. MiR-30-context Gpr65 shRNA were cloned into MSCV-PIG (IRES-GFP) vector (kindly provided by Dr. Mitchell Weiss) using Bgl II and Xho I restriction sites. Retrovirus expressing Gata2, containing a Gata2 cDNA, an empty vector, shRNA targeting luciferase, or Gpr65 were produced by co-transfecting 293T cells with pCL-Eco packaging vector. Retroviral supernatant was collected 24 h and 48 h post-transfection and centrifuged to remove cells and debris. The Retro-X™ Concentrator from Clontech (Cat. No. 631455) was used for concentrating retrovirus to get high-concentrated retrovirus. Briefly, the retroviral supernatant was mixed with the Retro-X™ Concentrator and rotated at 4° C. for 1h. The mixture was then centrifuged at 1,500 g for 45 minutes to obtain a high-titer virus-containing pellet which can be easily resuspended in $\frac{1}{100}^{th}$ of the original volume using IMDM Media (Iscove's modified Dulbecco's media) [Gibco] supplemented with 20% FBS [Gemini] and 1% penicillin/streptomycin [Cellgro].

Freshly isolated AGMs from E11.5 embryos were infected with 20 µl of high-concentrated retrovirus and 8 µg/ml polybrene in 500 µl of AGM explant culture media at 2800 rpm for 90 min at 30° C. After centrifugation, AGMs were subjected for AGM explant culture ex vivo.

Freshly isolated primary erythroid precursor cells were spinfected with 100 ul of retrovirus supernatant and 8 µg/ml polybrene in 400 µl of fetal liver expansion media at 2800 RPM for 90 min at 30° C. After centrifugation, 500 µl pre-warmed fetal liver expansion medium was added, and cells were incubated at 37° C. for 72 h.

```
miR-30-context Gpr65 shRNA sequence:
                                      (SEQ ID NO: 2)
TGCTGTTGACAGTGAGCGAGCAGGTTAAGTTACATGGTATTAGTGA

AGCCACAGATGTAATACCATGTAACTTAACCTGCCTGCCTACTGCC

TCGGA
```

Colony assay. FACS-sorted CD31$^+$c-Kit$^+$ cells from infected AGMs were plated in MethoCult™ M03434 complete medium (StemCell Technologies) in a 35 mm dish. After incubation in a humidified incubator at 37° C. with 5% carbon dioxide for 7 days, colonies were visualized by microscopy and quantitated. Cells isolated from colonies were subjected to Wright-Giemsa staining.

Quantitative real-time RT-PCR. Total RNA was purified from TRIzol® (Invitrogen) according to manufacturers' instructions. cDNA was synthesized from 1 μg purified total RNA by Moloney murine leukemia virus reverse transcriptase (M-MLV RT). Real-time PCR was performed with SYBR green master mix (Applied Biosystems) and Product accumulation was monitored by SYBR green fluorescence using either a StepOnePlus™ or Viia™7 instrument (Applied Biosystems). Relative expression was determined from a standard curve of serial dilutions of cDNA samples, and values were normalized to 18S RNA expression. The sequences of primers used for RT-PCR and genotyping are provided below.

Flow cytometry. Dissociated cells from cultured AGM explants were resuspended in PBS containing 2% FBS and passed through 25-μm cell strainers to obtain single-cell suspensions prior to antibody staining. Fetal liver cells were washed with PBS once before antibody staining. APC-conjugated antibody CD31 (MEC13.3, Biolegend), PE-conjugated antibody c-Kit (2B8, eBioscience), PerCP-Cy5.5-conjugated antibody Sca1 (D7, eBioscience), APC-conjugated antibody Ter119 (TER119, eBioscience) and PE-conjugated CD71 (R17217, eBioscience) were used for flow cytometry and Fluorescence Activated Cell Sorting (FACS). Samples were analyzed on a FACSAria™ II cell sorter (BD Biosciences). Cells were gated on GFP to ensure retroviral expression. DAPI (Sigma-Aldrich) exclusion was utilized for live/dead discrimination. FACS-sorted cells were immediately processed for RNA isolation or colony assay.

ChIP assay. Quantitative chromatin immunoprecipitation (ChIP) was conducted as previously described using antibodies specific for monomethylated H4K20 (Millipore), GATA-1, and Scl/TAL1. Samples were analyzed by quantitative real-time PCR using either a StepOnePlus™ or Viia™ 7 instrument (Applied Biosystems). The amount of product was determined relative to a standard curve generated from a serial dilution of input chromatin.

Statistical analysis. Student's t-tests were conducted using GraphPad Software or Microsoft Excel. For all figures, *: $p<0.05$; : $p<0.01$; *: $p<0.001$.

```
Primers.
+9.5 flanking forward:
                                (SEQ ID NO: 4)
5'-ATGTCCTTTCGGATCTCCTGCC-3'

+9.5 flanking reverse:
                                (SEQ ID NO: 5)
5'-GGTAAACAGAGCGCTACTCCTGTGTGTT-3'

18S rRNA forward:
                                (SEQ ID NO: 6)
5'-CGCCGCTAGAGGTGAAATTCT-3'

18S rRNA reverse:
                                (SEQ ID NO: 7)
5'-CGAACCTCCGACTTTCGTTCT-3'

Gata2 mRNA forward:
                                (SEQ ID NO: 8)
5'-GCAGAGAAGCAAGGCTCGC-3'

Gata2 mRNA reverse:
                                (SEQ ID NO: 9)
5'-CAGTTGACACACTCCCGGC-3'

Gpr65 mRNA forward:
                                (SEQ ID NO: 10)
5'-CAAGAGAAGCATCCCTCCAGAA-3'

Gpr65 mRNA reverse:
                                (SEQ ID NO: 11)
5'-TGTTTTTATTTTCACGCCGTTTG-3'

Gata2 primary transcript forward:
                                (SEQ ID NO: 12)
5'-GACATCTGCAGCCGGTAGATAAG-3'

Gata2 primary transcript reverse:
                                (SEQ ID NO: 13)
5'-CATTATTTGCAGAGTGGAGGGTATTAG-3'

MyoD promoter forward:
                                (SEQ ID NO: 14)
5'-GGGTAGAGGACAGCCGGTGT-3'

MyoD promoter reverse:
                                (SEQ ID NO: 15)
5'-GTACAATGACAAAGGTTCTGTGGGT-3'

Eif3k promoter forward:
                                (SEQ ID NO: 16)
5'-GTGATTTCCTTCCAGCAGTTGTAA-3'

Eif3k promoter reverse:
                                (SEQ ID NO: 17)
5'-CTCACGCTATTGGTCTCTTTTAAGTG-3'

Gata2_9.5 Site_933 bp forward:
                                (SEQ ID NO: 18)
5'-CTTGCTGCTGGCTCTGAGAAC-3'

Gata2_9.5 Site_933 bp reverse:
                                (SEQ ID NO: 19)
5'-AGTCCAGGGTCTTTTAAGGATAAATTC-3'

Gata2_9.5 Site_480 bp forward:
                                (SEQ ID NO: 20)
5'-AACCTTCAAATGCAGACACTTCAC-3'

Gata2_9.5 Site_480 bp reverse:
                                (SEQ ID NO: 21)
5'-GAATCCGCCAGAACGAAGAC-3'

Gata2_9.5 Site forward:
                                (SEQ ID NO: 22)
5'-GACATCTGCAGCCGGTAGATAAG-3'

Gata2_9.5 Site reverse:
                                (SEQ ID NO: 23)
5'-CATTATTTGCAGAGTGGAGGGTATTAG-3'

Gata2_9.5 Site_446 bp forward:
                                (SEQ ID NO: 24)
5'-GCCGAGGGAGTTCAGTGCTA-3'

Gata2_9.5 Site_446 bp reverse:
                                (SEQ ID NO: 25)
5'-AGCGCTACTCCTGTGTGTTCTTC-3'

Gata2_9.5 Site_880 bp forward:
                                (SEQ ID NO: 26)
5'-TCCTGGCGACTCCTAGATCCTA-3'

Gata2_9.5 Site_880 bp reverse:
                                (SEQ ID NO: 27)
5'-GAAAGCCCTGAGGAAGTTGGA-3'

Lyl1 Exon 1 forward:
                                (SEQ ID NO: 28)
5'-TCAGCATTGCTTCTTATCAGCC-3'

Lyl1 Exon 1 reverse:
                                (SEQ ID NO: 29)
5'-CGCAGAGGCCAGAGGATG-3'

Kit_114 kb forward:
                                (SEQ ID NO: 30)
5'-GCACACAGGACCTGACTCCA-3'
```

-continued

Kit_114 kb reverse:
(SEQ ID NO: 31)
5'-GTTCTGAGATGCGGTTGCTG-3'

Hdc mRNA forward:
(SEQ ID NO: 32)
5'-ACCTCCGACATGCCAACTCT-3'

Hdc mRNA reverse:
(SEQ ID NO: 33)
5'-CCGAATCACAAACCACAGCTT-3' c-Kit mRNA forward:
(SEQ ID NO: 34)
5'-AGCAATGGCCTCACGAGTTCTA-3' c-Kit mRNA reverse:
(SEQ ID NO: 35)
5'-CCAGGAAAAGTTTGGCAGGAT-3'

Lyl1 mRNA forward:
(SEQ ID NO: 36)
5'-AAGCGCAGACCAAGCCATAG-3'

Lyl1 mRNA reverse:
(SEQ ID NO: 37)
5'-AGCGCTCACGGCTGTTG-3' c-Myb mRNA forward:
(SEQ ID NO: 38)
5'-CGAAGACCCTGAGAAGGAAA-3' c-Myb mRNA reverse:
(SEQ ID NO: 39)
5'-GCTGCAAGTGTGGTTCTGTG-3'

Runx1 mRNA forward:
(SEQ ID NO: 40)
5'-TCACTGGCGCTGCAACAA-3'

Runx1 mRNA reverse:
(SEQ ID NO: 41)
5'-TCTGCCGAGTAGTTTTCATCGTT-3'

TAL1 mRNA forward:
(SEQ ID NO: 42)
5'-GAGGCCCTCCCCATATGAGA-3'

TAL1 mRNA reverse:
(SEQ ID NO: 43)
5'-GCGCCGCACTACTTTGGT-3'

Sfpi1 mRNA forward:
(SEQ ID NO: 44)
5'-GGCAGCGATGGAGAAAGC-3'

Sfpi1 mRNA reverse:
(SEQ ID NO: 45)
5'-GGACATGGTGTGCGGAGAA-3'

Figure 1B:
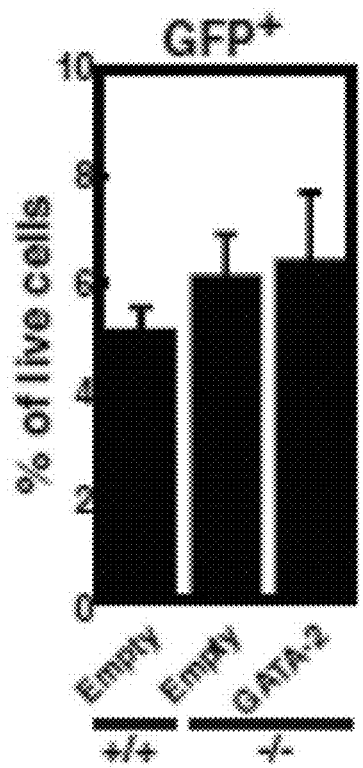
Figure 1C:
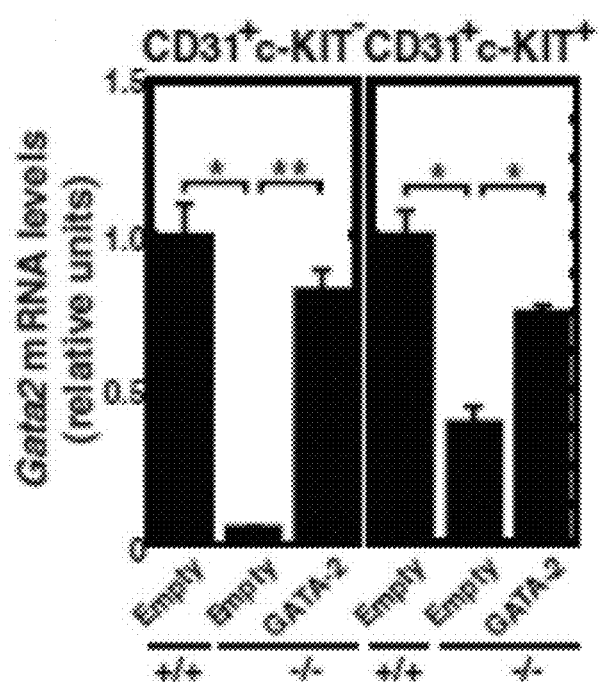
Figure 1D:
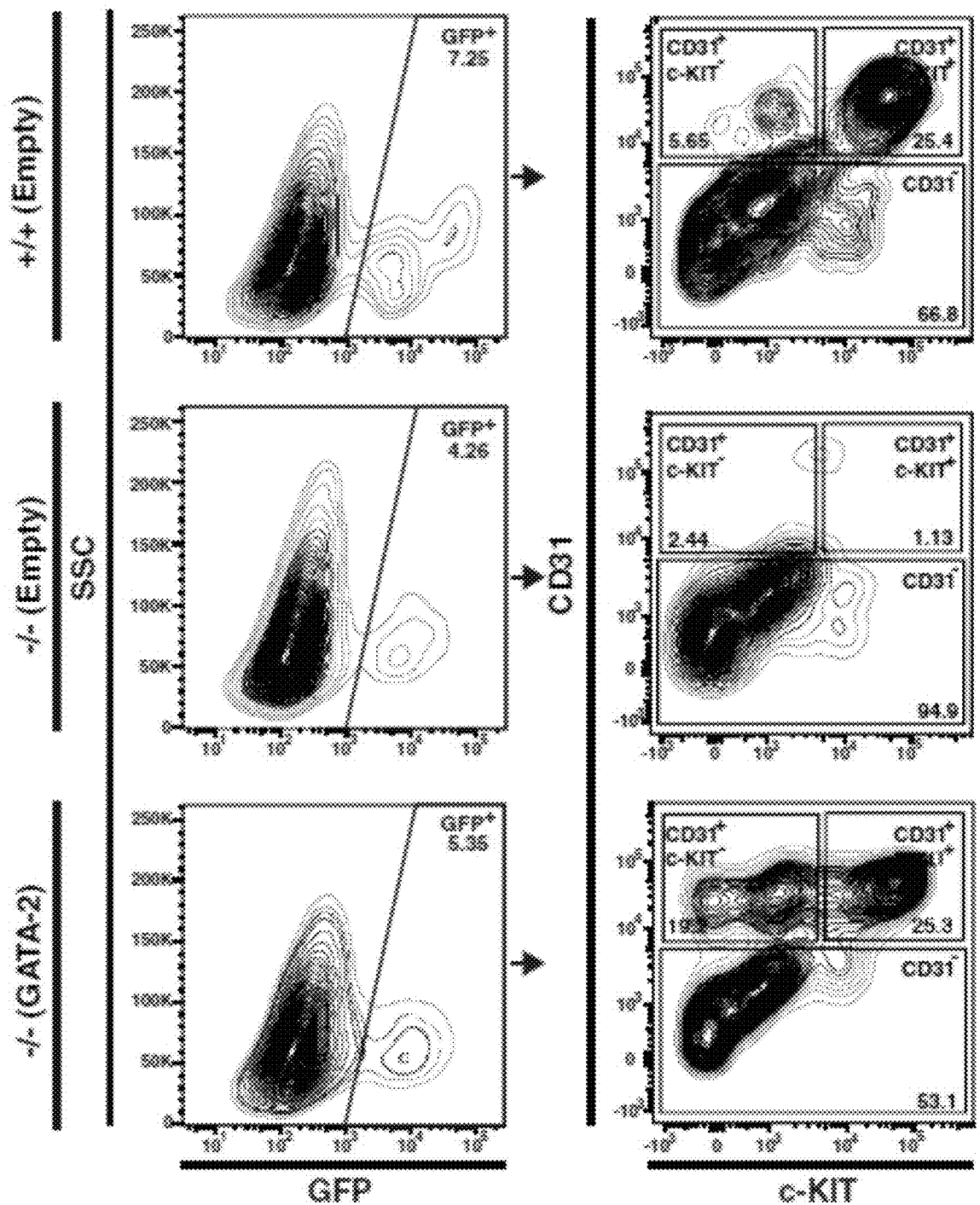
Figure 1E:
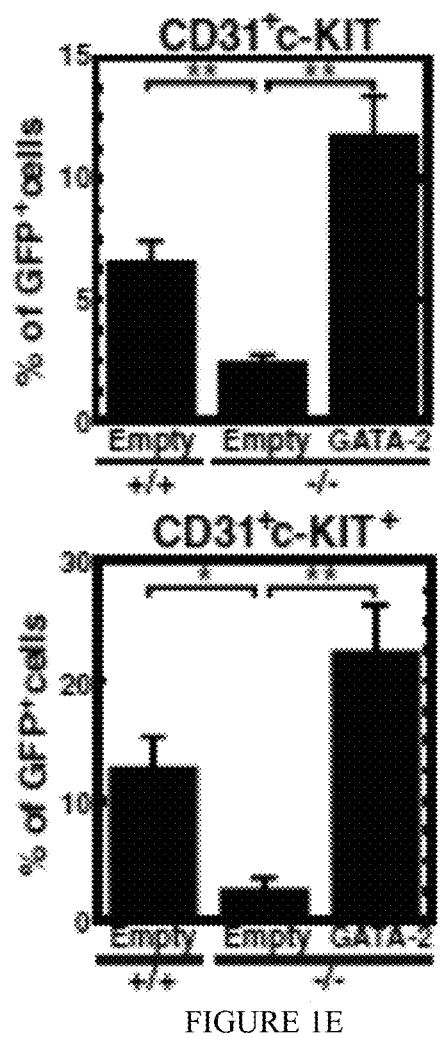
Figure 1F:
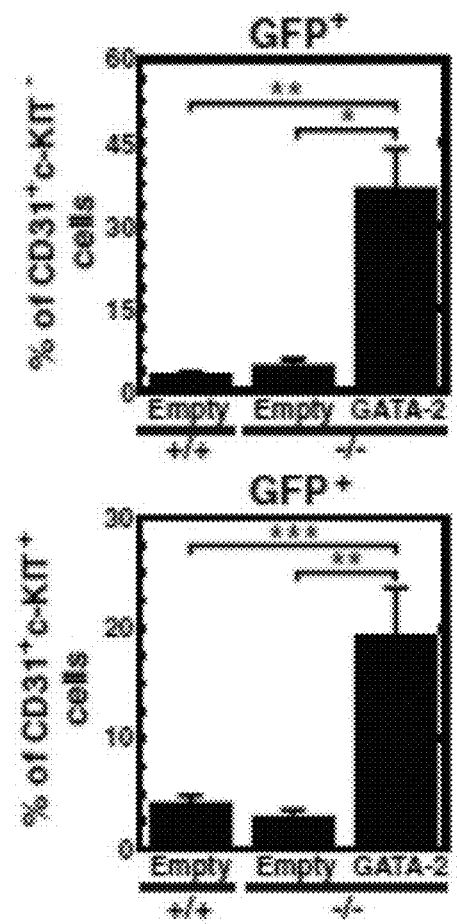

Example 1: GATA-2 Expression in +9.5$^{-/-}$ AGM Rescues Hematopoietic Cell Generation Deletion of the +9.5 site reduced Gata2 expression in AGM hemogenic endothelium and abrogated EHT (FIG. 1A). These results suggest that factors/signals conferring +9.5 activity control Gata2 expression, which promotes EHT. In principle, the +9.5 might regulate other genes in cis or in trans that control EHT. To determine if the HSC generation defect of +9.5$^{-/-}$ AGM results from insufficient GATA-2 production, we tested whether GATA-2 expression rescues the defect. E11.5 mouse embryo AGMs were infected with GATA-2-expressing retrovirus (FIG. 1A). After 96 h of explant culture, we quantitated endothelial and hematopoietic cell populations in infected (GFP$^+$) cells by flow cytometry using CD31 and c-KIT surface markers. The infection efficiency was similar among the three conditions (+9.5$^{+/+}$-empty vector, +9.5$^{-/-}$-empty vector, +9.5$^{-/-}$-GATA-2), as indicated by the indistinguishable percentage of GFP$^+$live cells (FIG. 1B). GATA-2 expression restored Gata2 mRNA to the wild type level in CD31$^+$c-KIT$^-$ endothelial and CD31$^+$c-KIT$^+$ hematopoietic cells (FIG. 1C), and rescued both populations (FIGS. 1D and 1E). Since the infected cells express GFP, the percentage of GFP$^+$ cells in each population increased in +9.5$^{-/-}$ AGM infected with GATA-2-expressing retrovirus (FIG. 1F). However, retroviral-mediated GATA-2 expression did not rescue CD31$^+$c-KIT$^-$ endothelial and CD31$^+$c-KIT$^+$ hematopoietic cell populations in the GFP$^-$ cells (data not shown). Thus, the +9.5$^{-/-}$ AGM hematopoiesis defect resulted from insufficient GATA-2 production, is associated with reduced CD31$^+$c-KIT$^-$ endothelial cells, and can be rectified by restoring GATA-2.

Figure 2A:
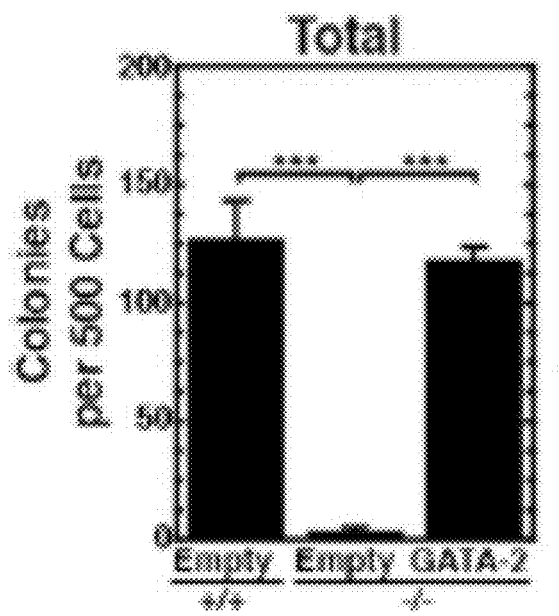
FIGS. 2 A-D show rescued CD31$^+$c-Kit$^+$ cells exhibit normal colony-forming unit activity. (A and B) Quantitative analysis of colony-forming activity of FACS-sorted CD31$^+$c-KIT$^+$ cells (6 litters: +9.5$^{+/+}$-Empty [n=9 embryos]; +9.5$^{-/-}$-Empty [n=7 embryos]; +9.5$^{-/-}$-GATA-2 [n=10 embryos]). (C) Representative BFU-E, CFU-GM, and CFU-GEMM colonies from FACS-sorted CD31$^+$c-KIT$^+$ cells. Scale bar, 2 mm. (D) Representative images of Wright-Giemsa stained cells obtained from colonies. Mac, macrophage; Ery, erythroblast; Neu, neutrophil; Mye, myeloid precursor. Scale Bar, 40 μm. Error bars represent SEM. *, P<0.05; , P<0.01; *, P<0.001 (two-tailed unpaired Student's t-test).
Figure 2B:
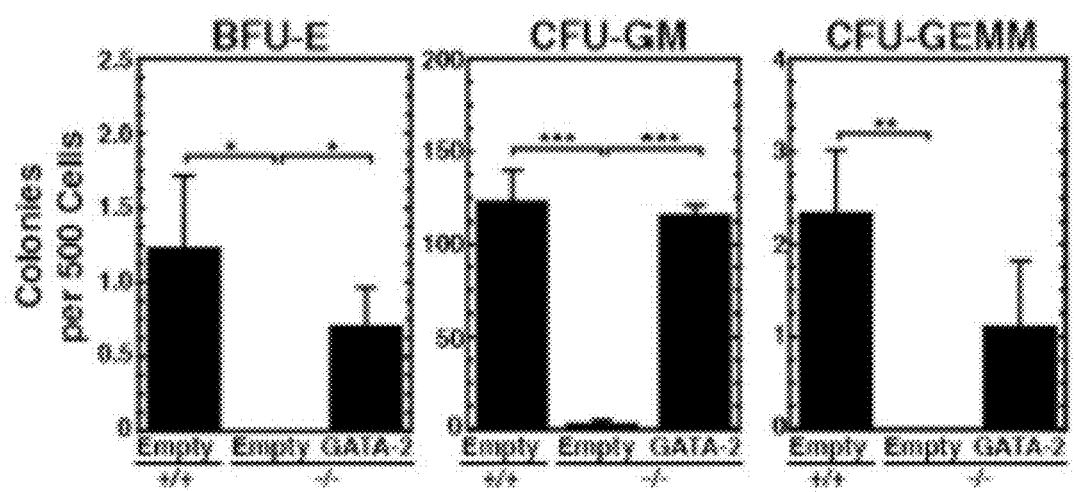
Figure 2C:
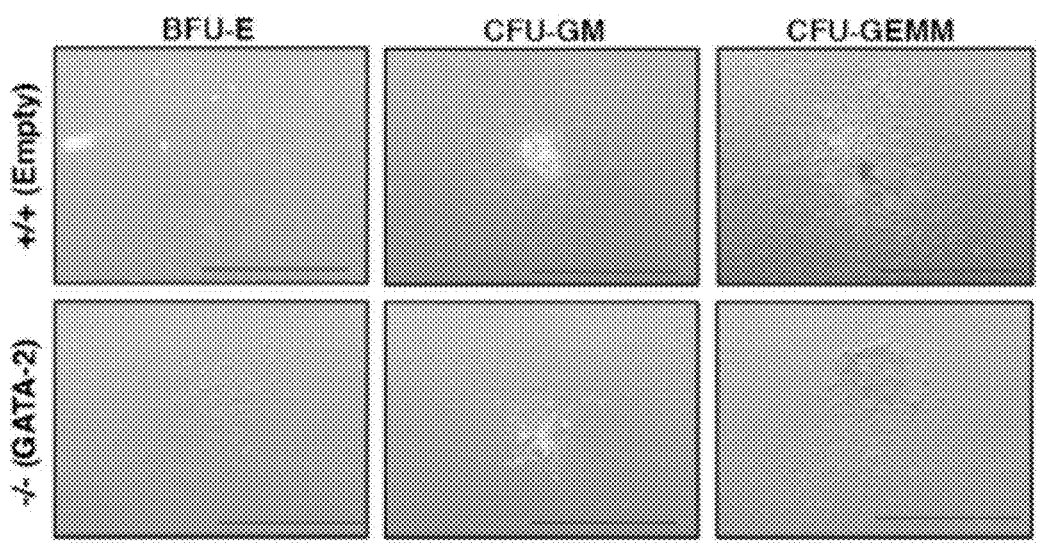
Figure 2D:
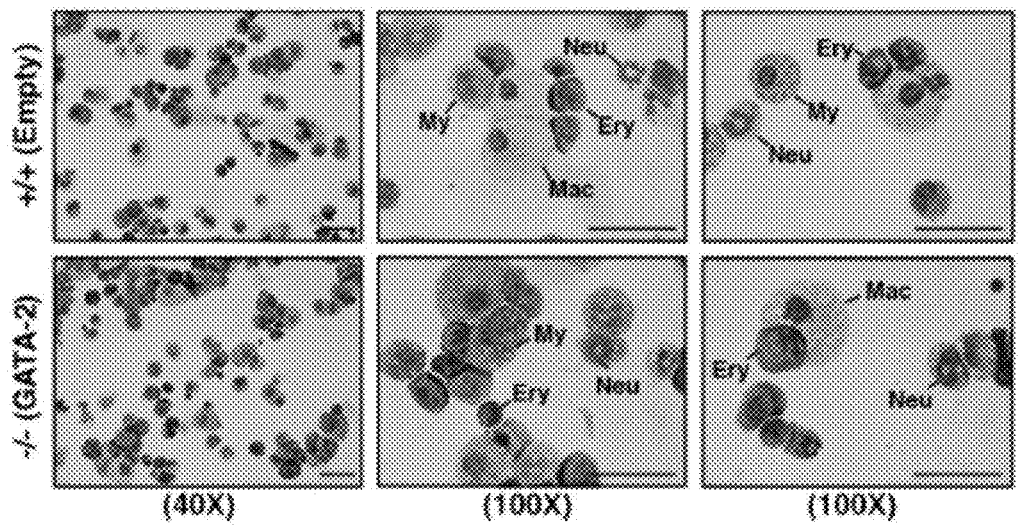

To assess whether the GATA-2-rescued CD31$^+$c-KIT$^+$ hematopoietic cells are functional, their capacity to generate myelo-erythroid colonies in a Colony Forming Unit (CFU) assay was determined. After culturing retroviral-infected AGMs for 96 h, GFP$^+$ CD31$^+$c-KIT$^+$ hematopoietic cells were isolated by fluorescence activated cell sorting (FACS) and assayed for their capacity to generate BFU-E, CFU-GM and CFU-GEMM colonies. Whereas +9.5$^{-/-}$ AGM failed to generate CFUs, GATA-2 expression in the +9.5$^{-/-}$ AGM induced CFUs comparable to +9.5$^{+/+}$ AGM (FIG. 2A). Quantification of colony types revealed comparable numbers of rescued CFU-GM colonies in comparison with wild type AGM (FIG. 2B). GATA-2 expression induced BFU-E and CFU-GEMM colonies (FIG. 2B). Colonies derived from wild type and rescued samples were morphologically indistinguishable (FIG. 2C). Wright-Giemsa staining of cells from colonies revealed normal myeloid and erythroid cell generation from the GATA-2-expressing +9.5$^{-/-}$ AGM (FIG. 2D). The GATA-2-induced CD31$^+$c-KIT$^+$ hematopoietic cells exhibited qualitatively and quantitatively normal activity.

Figure 3A:
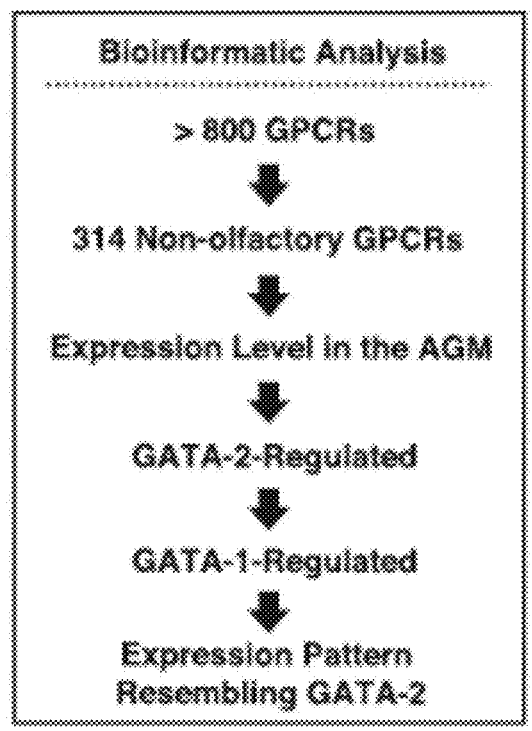
FIGS. 3 A-L show Global GPCR analysis in the AGM. (A) Schematic diagram showing global GPCR analysis strategy. (B) A total of 314 non-olfactory GPCRs were categorized into Secretin, adhesion, Glutamate, Frizzled/Taste2 and Rhodopsin families based on sequence homology. (C) Classification of 85 GPCRs expressed in the AGM (>5 transcripts per million/TPM) into 5 families. (D) Bar graph depicting statistically significant genes regulated by GATA-2 from RNA-seq analysis of +9.5$^{+/+}$ and +9.5$^{-/-}$ AGMs (Gao et al., 2013). Black bars indicate genes co-regulated by GATA-1 according to our prior microarray analysis of G1E-ER-GATA W/O β-estradiol treatment. (E) Expression pattern of Gata2, Adora3, Gpr65, Ltb4r1, and P2ry1 during erythropoiesis (P: Proerythroblast, B: Basophilic Erythroblast, O: Polyorthochromatic Erythroblast, and R: Reticulocyte). (F) Time course of Gata2 and Gpr65 expression following estradiol treatment in G1E-ER-GATA cells (n=3 independent experiments). (G) RT-PCR analysis of Gata2 and Gpr65 in FACS-sorted R1, R2, R3, and R4/5 populations from fetal liver (n=3 independent experiments). (H and I) ChIP signal map for Gpr65 in human CD34 cells (H), mouse HPC7 cells, Lin$^-$ bone marrow cells, and G1E cells (I). (J and K) RT-PCR analysis of Gata2 and Gpr65 mRNA in +9.5$^{+/+}$ and +9.5$^{-/-}$ AGM (5 litters: +9.5$^{+/+}$ [n=8 embryos]; +9.5$^{-/-}$ [n=6 embryos]) and Yolk sac (3 litters: +9.5$^{+/+}$ [n=7 embryos]; +9.5$^{-/-}$ [n=5 embryos]) (J), and MAE cells expressing GATA-2 (K) (n=3 independent experiments). (L) RNA-seq analysis of Gata2 and Gpr65 mRNA in FACS-sorted EC, HEC, HC, and HSCs from the AGM. EC: endothelial cells; HEC: hemogenic endothelial cells; HC: hematopoietic cell; HSC: hematopoietic stem cells. Error bars represent SEM. *, P<0.05 (two-tailed unpaired Student's t-test).
Figure 3B:
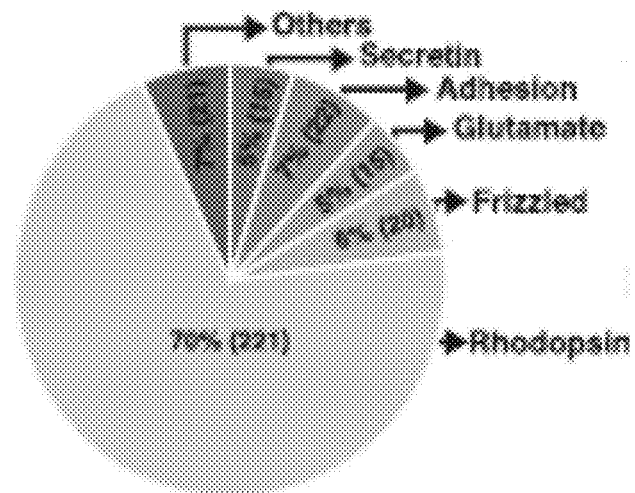

Example 2: Global GPCR Analysis in the AGM: Discovery of a GATA Factor-Regulated GPCR Cohort The +9.5 site confers Gata2 expression and establishes a genetic network involving known HSC regulators and genes not implicated in hematopoiesis. To discover vital constituents of the network, especially those with potential for modulation by small molecules/drugs, we systematically analyzed the expression pattern of non-olfactory GPCRs (FIG. 3A). The human genome encodes greater than 800 GPCRs, which are categorized into rhodopsin, secretin, glutamate, adhesion and frizzed/taste2 families based on sequence homology; 341 are distinct from the olfactory and taste GPCRs. Using AGM RNA-seq data, we parsed AGM-expressed GPCRs into the canonical categories: secretin, 5% (15); adhesion, 7% (22); glutamate, 5% (15); frizzled/taste2, 6% (20); and rhodopsin, 70% (221) (FIG. 3B).

Figure 3C:
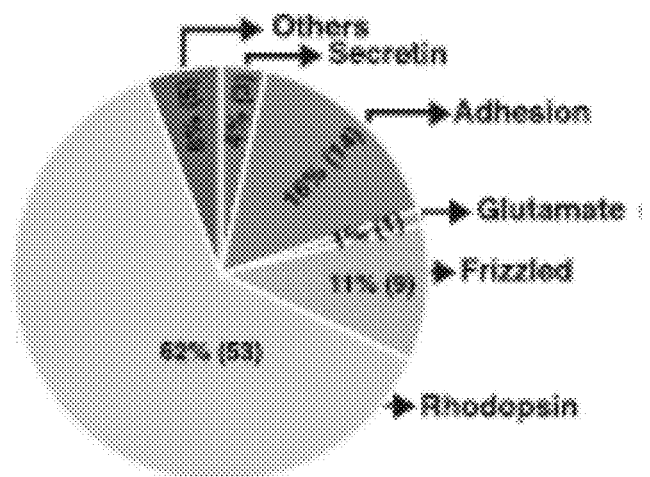
Figure 3D:
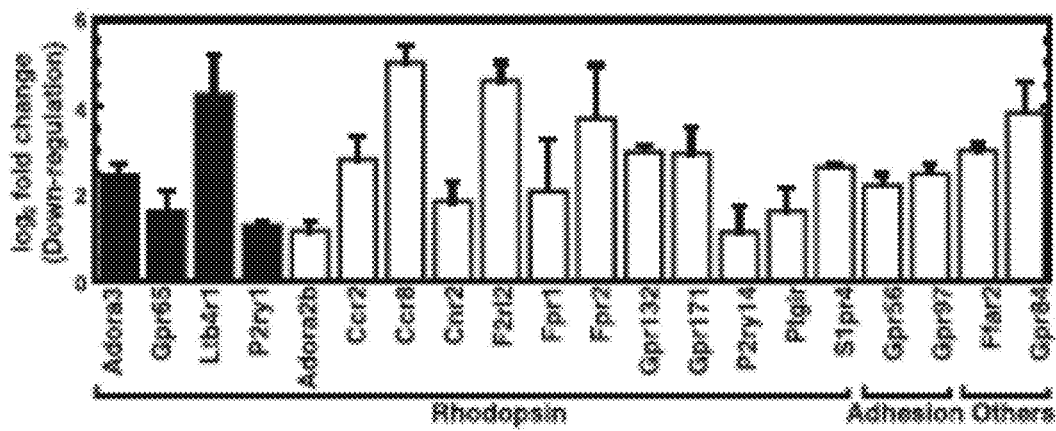

To discover GPCRs that control HSC generation and/or activity, we evaluated GPCR expression in the AGM. Of the 314 GPCRs annotated by RNA-seq, 85 were expressed at >5 transcripts per million (TPM) (FIG. 3C), a level that can be validated with high frequency by real-time RT-PCR. Of the 85 GPCRs, 20 were downregulated in the +9.5$^{-/-}$ AGM versus +9.5$^{+/+}$ AGM (FIG. 3D), indicating GATA-2-regulation. Using our previous microarray dataset (untreated or β-estradiol-treated G1E-ER-GATA-1 erythroid precursor cells), we found that 4 of the 20 GATA-2-regulated GPCRs were GATA-1-regulated (FIG. 3D). Our strategy refined the 314 non-olfactory, AGM-expressed GPCRs to yield Adora3, Gpr65, Ltb4r1, and P2ry1, which are GATA-2- and GATA-1-regulated.

Example 3: A GATA Factor-GPCR Feedforward Loop Suppresses AGM Hematopoiesis

Figure 3E:
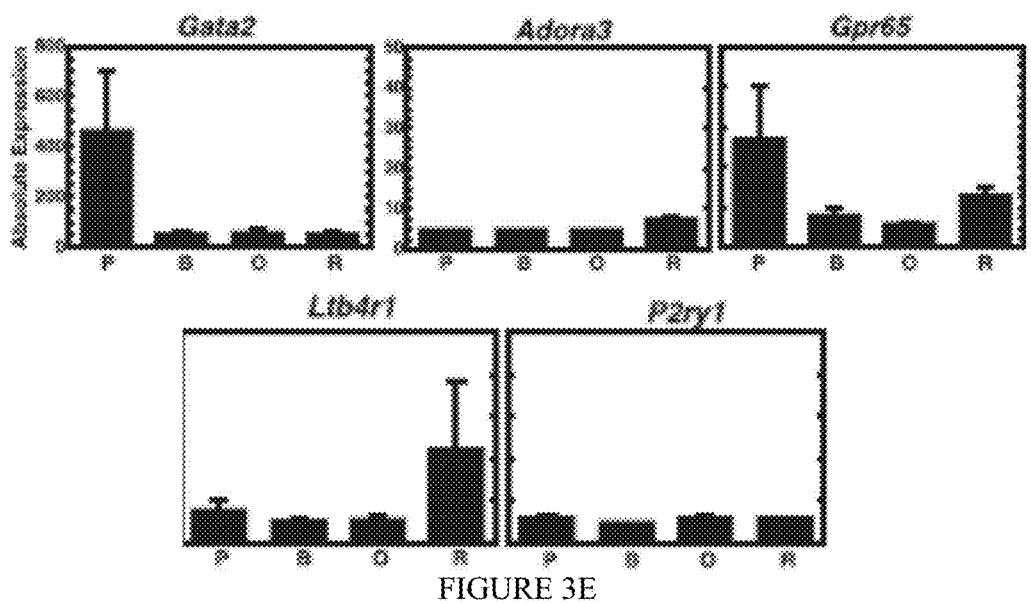
Figure 3F:
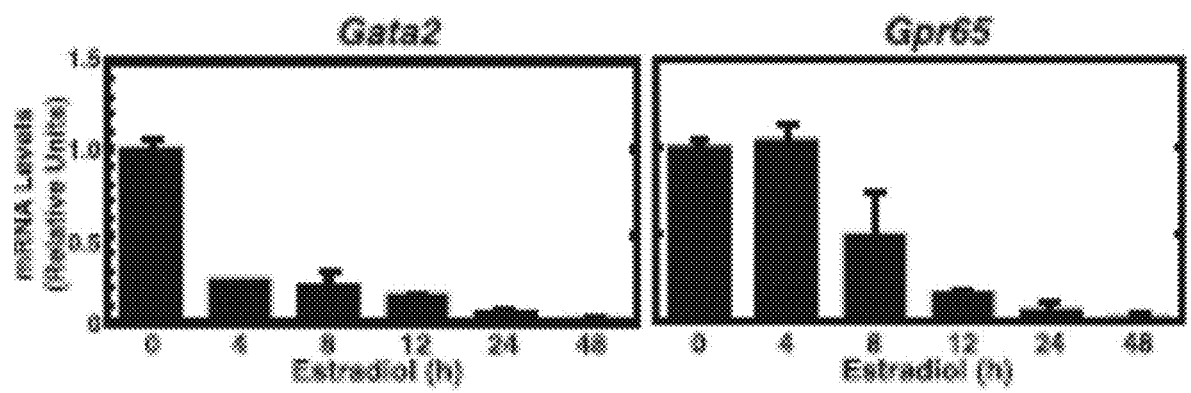
Figure 3G:
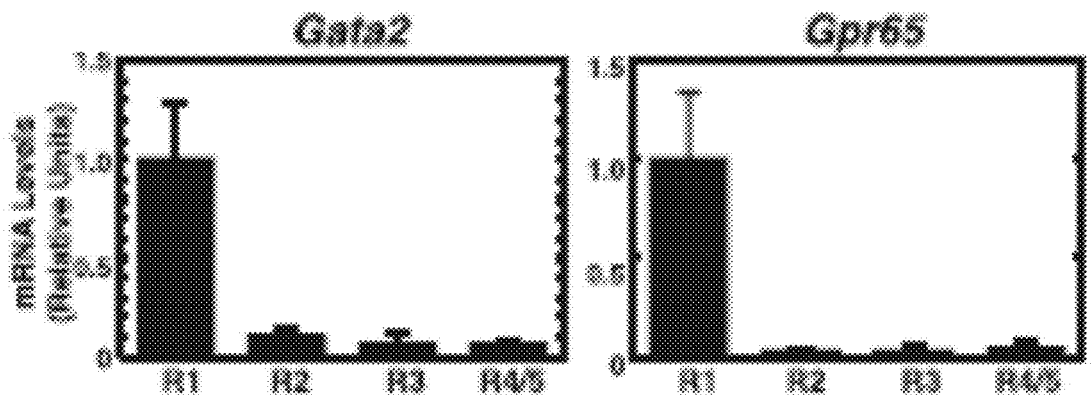
Figure 3H:
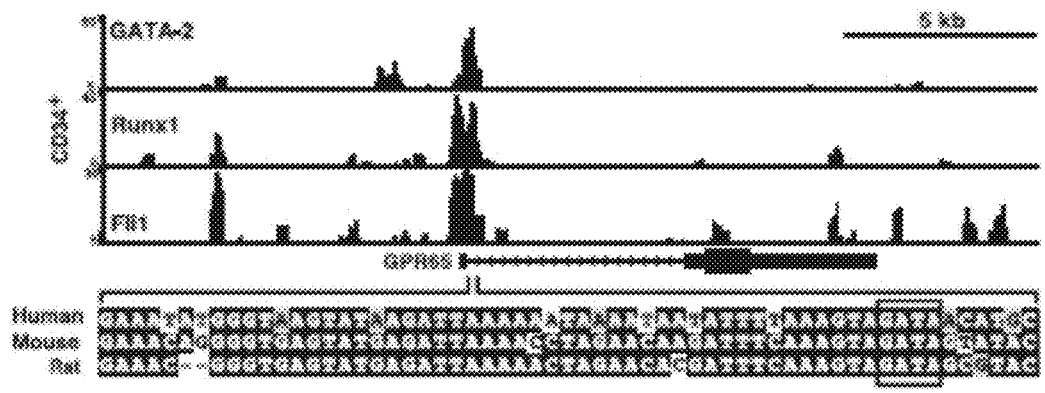
Figure 3I:
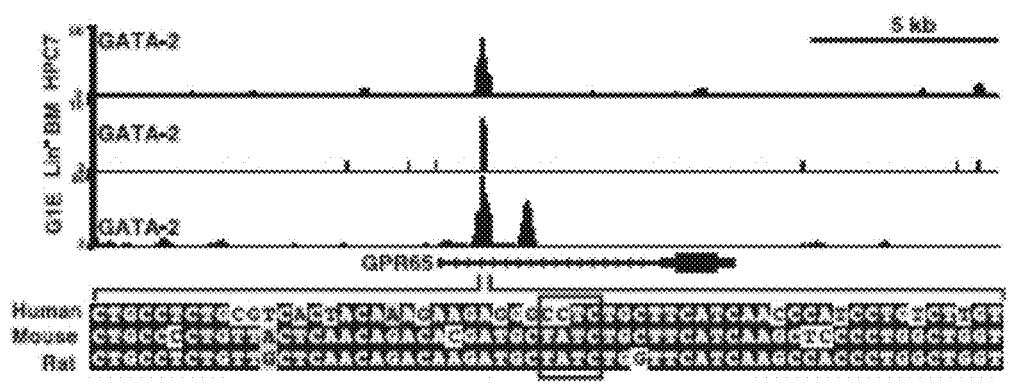
Figure 3J:
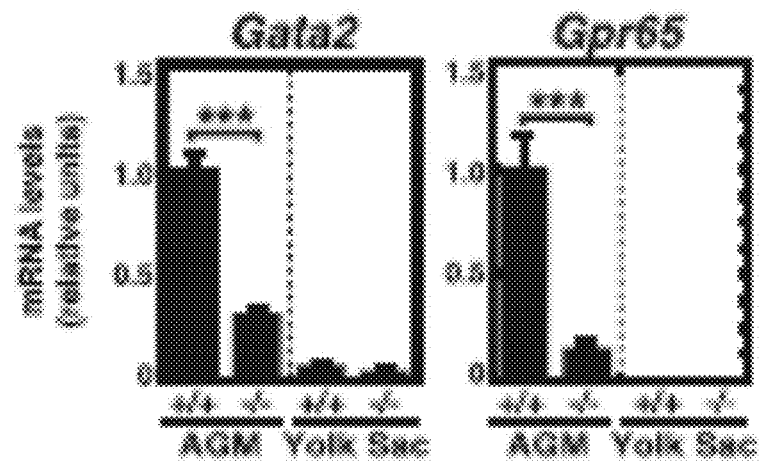
Figure 3K:
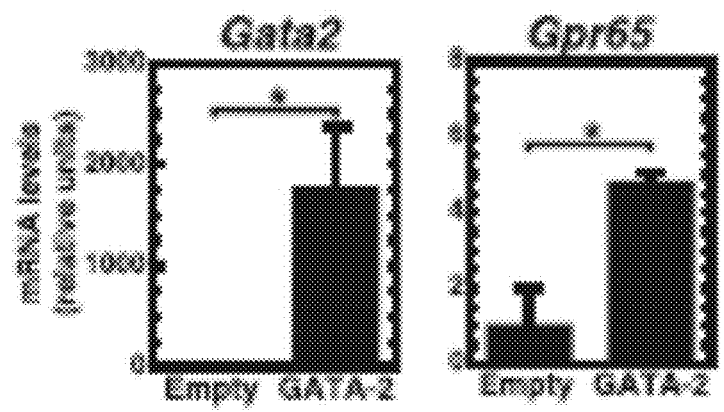
Figure 3L:
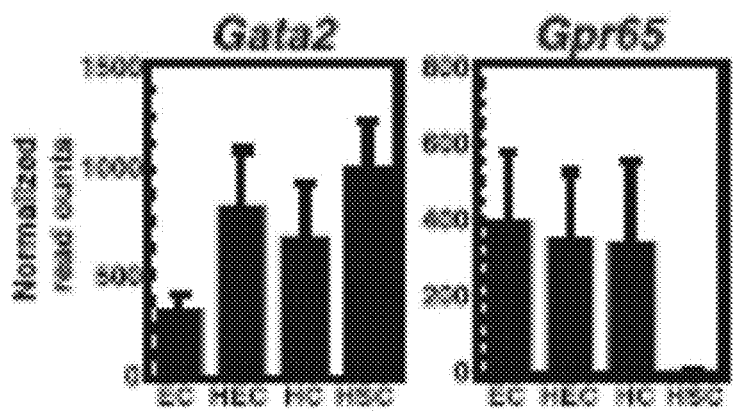

As shared gene expression patterns can infer functional interconnectivity, we compared Adora3, Gpr65, Ltb4r1, P2ry1, and Gata2 expression patterns in mouse cells and tissues. Only Gpr65 resembled Gata2, both being expressed in HSPCs and mast cells (data not shown). As GATA-1 represses Gata2 during erythroid maturation via a GATA switch, Gata2 expression declines upon erythroid maturation. Mining the Erythron Database, which provides transcriptomics data during erythroid precursor cell maturation into erythrocytes, revealed Gata2 and Gpr65 repression upon erythroid differentiation. Gpr65 was the only one of the four GPCR genes to have a Gata2-like expression pattern (FIG. 3E). To further compare expression patterns, we quantitated Gata2 and Gpr65 mRNA in G1E-ER-GATA-1 cells treated with β-estradiol to induce erythroid maturation and in FACS-sorted R1, R2, R3 and R4/5 fetal liver cell populations. Gpr65 and Gata2 were repressed during erythroid maturation (FIGS. 3F and 3G). These correlations are consistent with GATA-2 upregulating Gpr65 expression in the AGM and may point to a functional link between GATA-2 and GPR65. ChIP-seq analysis in human (FIG. 3H) and mouse (FIG. 3I) cells revealed GATA-2 occupancy at Gpr65, suggesting that GATA-2 directly regulates Gpr65 transcription. Comparison of $+9.5^{+/+}$ and $+9.5^{-/-}$ AGM revealed that reduced Gata2 expression in the $+9.5^{-/-}$ AGM decreased Gpr65 expression, and Gpr65 expression was undetectable in the yolk sac (FIG. 3J). Previously, we demonstrated that GATA-2 expression in Mouse Aortic Endothelial cells increases transcription of certain GATA-2 target genes. In this system, GATA-2 increased Gpr65 expression (FIG. 3K), indicating that GATA-2 regulates Gpr65 expression in multiple contexts. To analyze the Gpr65 expression pattern in distinct cell types within the AGM, we mined RNA-seq data obtained with FACS-sorted endothelial cells (EC), hemogenic endothelial cells (HEC), hematopoietic cells (HC) and hematopoietic stem cells (HSC) from the AGM (Solaimani Kartalaei et al., 2015). This analysis revealed that Gpr65 is detectable in all cell types, and the levels are lower in HSCs (FIG. 3L).

Figure 4A:
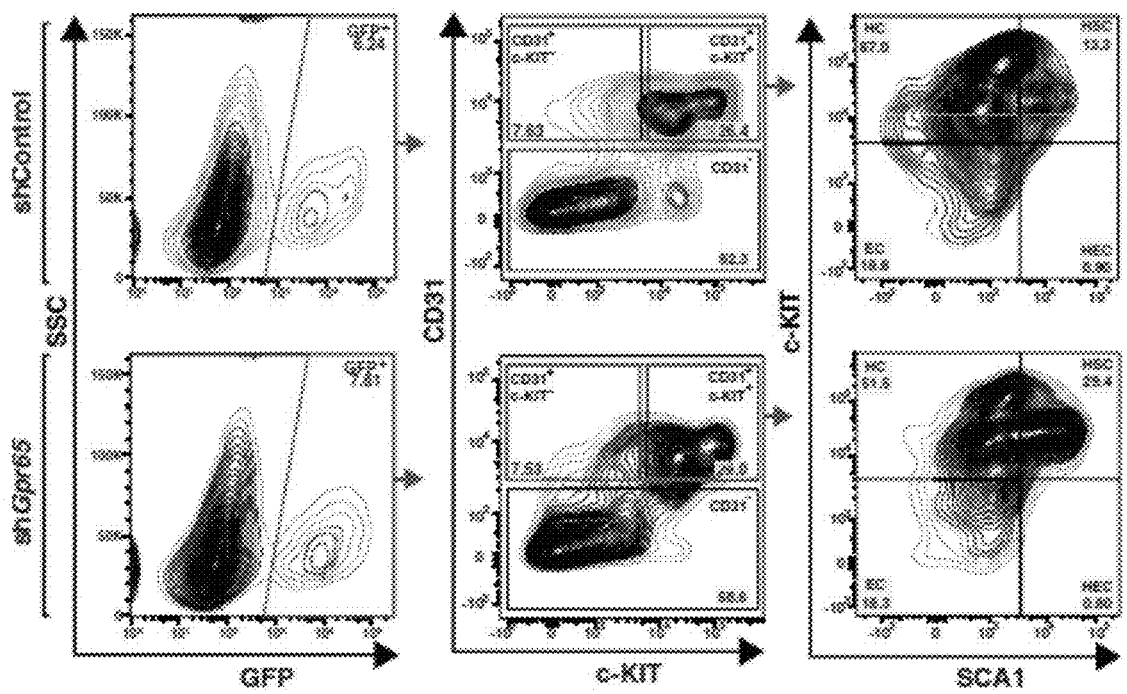
FIGS. 4 A-G show Gpr65 suppresses hematopoiesis in the AGM and zebrafish. (A) Representative plots from flow cytometric analysis of CD31$^+$c-MT$^+$ and CD31$^+$c-KIT$^+$ SCA1$^+$ cell populations in control or Gpr65 shRNA treated AGMs after 96 h of culture. (B) Quantitation of GFP$^+$ cells within total live cells (9 litters: shLuc [n=22 embryos]; shGpr65 [n=26 embryos]). (C) RT-PCR analysis of Gpr65 mRNA levels in FACS-sorted GFP$^+$ cells (6 lifters: shLuc [n=15 embryos]; shGpr65 [n=15 embryos]). (D and E) Analysis of flow cytometry data expressed as the percentage of CD31$^+$c-KIT$^+$ (D) and CD31$^+$c-KIT$^+$ Scal1$^+$ (E) cells in GFP$^+$ cells (D: 9 lifters: shLuc [n=22 embryos]; shGpr65 [n=26 embryos]; E: 7 litters: shLuc [n=18]; shGpr65 [n=22]). (F) Representative images of ISH with the HSC markers Runx1/cMyb at 36 h post-fertilization. (G) Quantitation of ISH data expressed as percentage of embryos with high, medium, and low Runx1/cMyb staining in total embryos (ATG MO 0 ng [124 embryos]; ATG MO 4 ng [75 embryos]; ATG MO 6 ng [66 embryos]; SP MO 0 ng [97 embryos]; SP MO 4 ng [49 embryos]; SP MO 6 ng [58 embryos]). Gpr65_ATG MO: morpholino targeting the translation start site of Gpr65; Gpr65_SP MO: morpholino blocking the splicing of Gpr65. Error bars represent SEM. *, P<0.05; ***, P<0.001 (two-tailed unpaired Student's t-test).
Figure 4B:
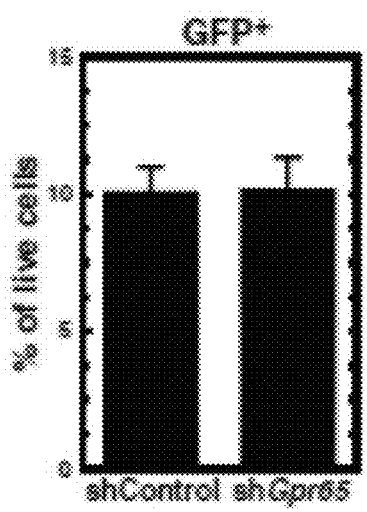
Figure 4C:
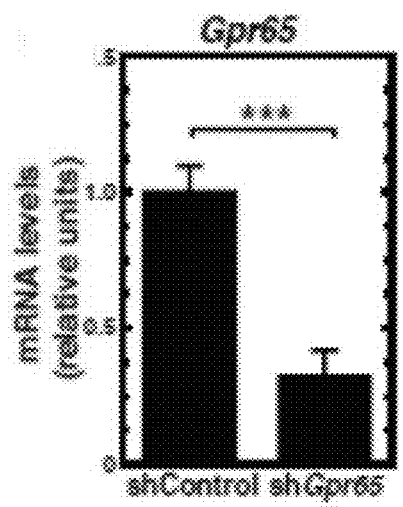
Figure 4D:
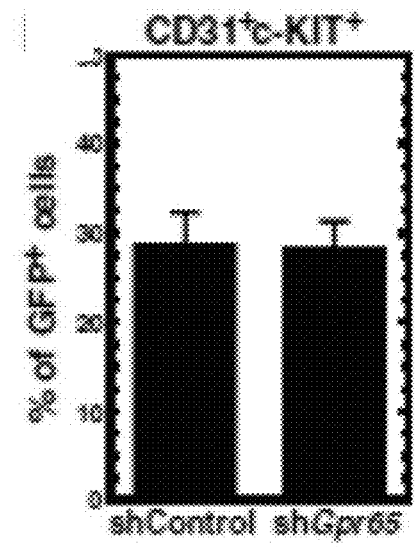
Figure 4E:
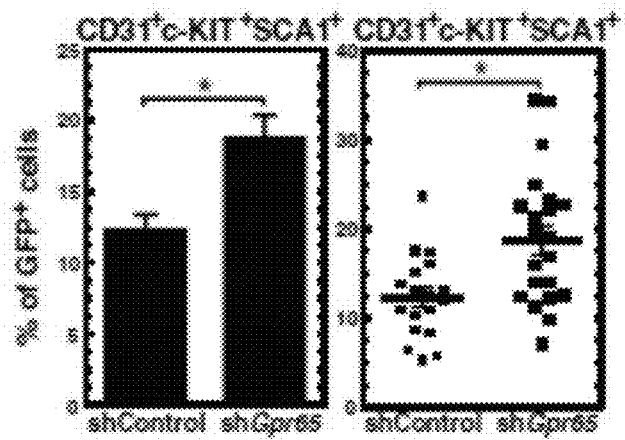

To test whether GPR65 controls hematopoiesis in the AGM, we conducted a loss-of-function analysis using a Gpr65 shRNA retrovirus. E11.5 AGMs were infected, and after culturing for 96 h, hematopoietic cell populations were quantitated by flow cytometry. Quantitation of GFP$^+$ live cells indicated that control shRNA (shLuc) and shGpr65 retroviruses had an indistinguishable infection efficiency (FIGS. 4A and 4B). Gpr65 knockdown reduced Gpr65 mRNA by 60-70% (FIG. 4C). While downregulating Gpr65 did not alter CD31$^+$c-KIT$^+$ hematopoietic cells (FIGS. 4A and 4D), it increased CD31$^+$c-KIT$^+$SCA1$^+$ HSC-containing, multipotent hematopoietic cells (FIGS. 4A and 4E). Retroviral-mediated Gpr65 shRNA expression did not alter CD31$^+$c-KIT$^+$ hematopoietic cells and CD31$^+$c-KIT$^+$SCA1$^+$ HSC-containing cells in GFP$^-$ cells (data not shown). These results indicate that GPR65 suppresses hematopoiesis in the AGM.

Figure 4F:
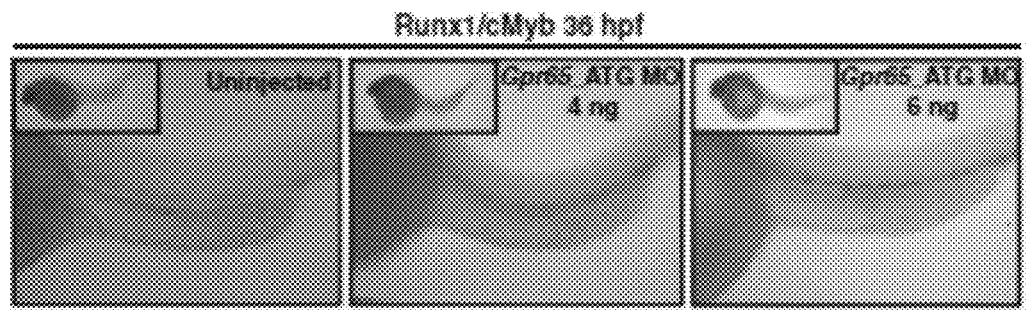
Figure 4G:
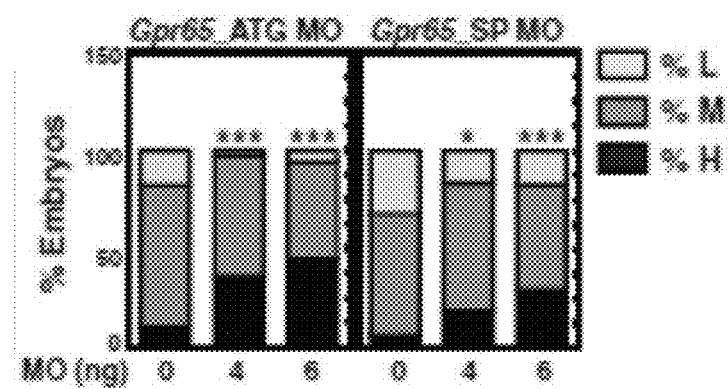
Figure 5A:
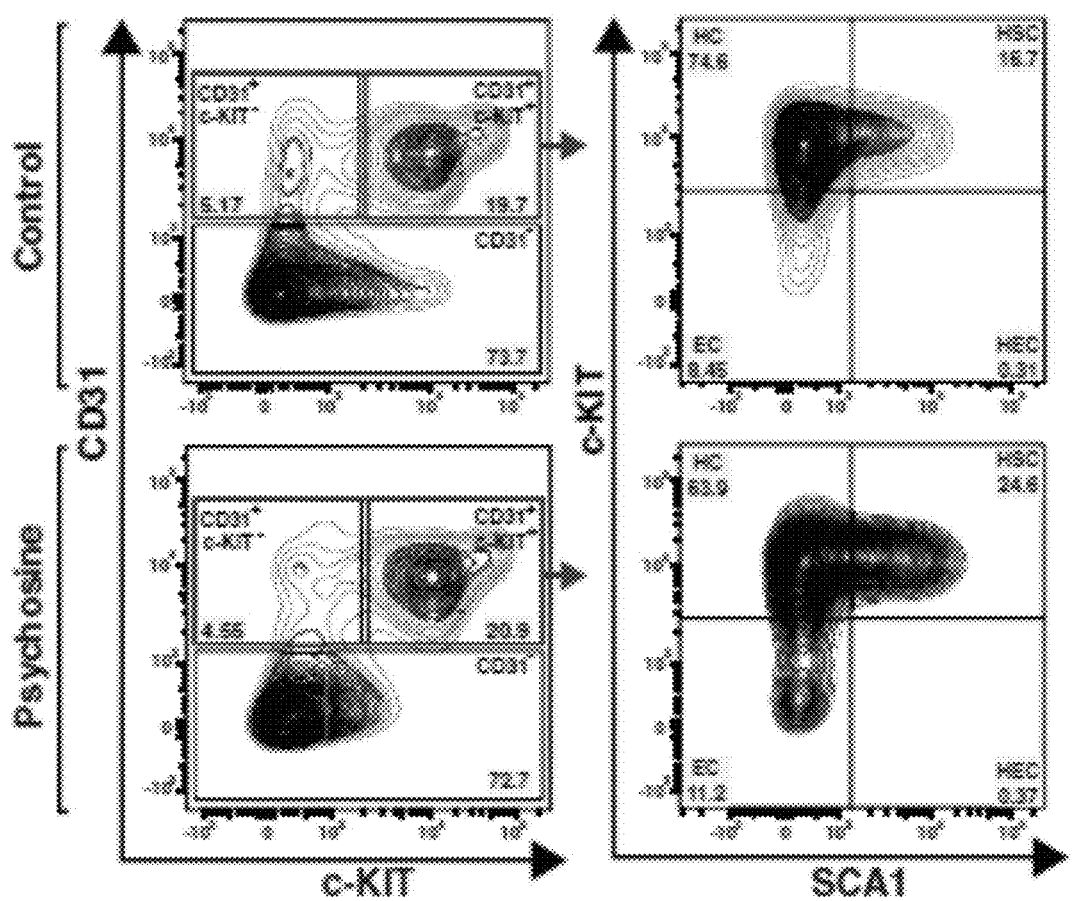
FIGS. 5 A-E show that psychosine promotes hematopoiesis in the AGM and GPR65 suppresses hematopoiesis by repressing Gata2 expression. (A) Representative flow cytometric plots of CD31$^+$c-KIT$^+$ and CD31$^+$c-KIT$^+$SCA1$^+$ cell populations in the AGM after 4 days of culture with 20 μM psychosine. (B and C) The average percentage of CD31$^+$c-KIT$^+$ (B) and CD31$^+$c-KIT$^+$SCA1$^+$ (C) cell populations with vehicle or psychosine treatment (6 litters: control [n=19 embryos]; psychosine [n=20 embryos]). (D and E) RT-PCR analysis of Gpr65, Gata2, and Runx1 mRNA (D) and Gata2 primary transcript (E) in FACS-sorted CD31$^+$c-KIT$^-$ cells (n=3 independent experiments). Error bars represent SEM. *, P<0.05; , P<0.01; *, P<0.001 (two-tailed unpaired Student's t-test).
Figure 5B:
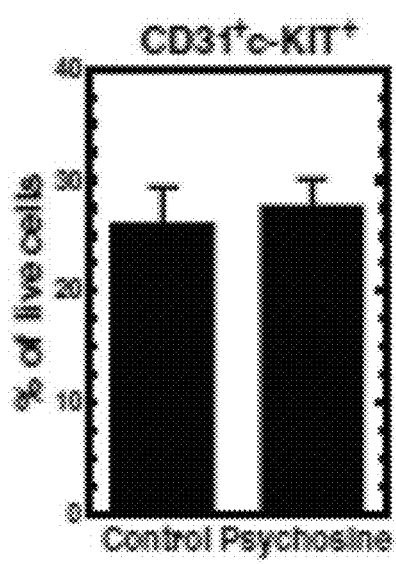
Figure 5C:
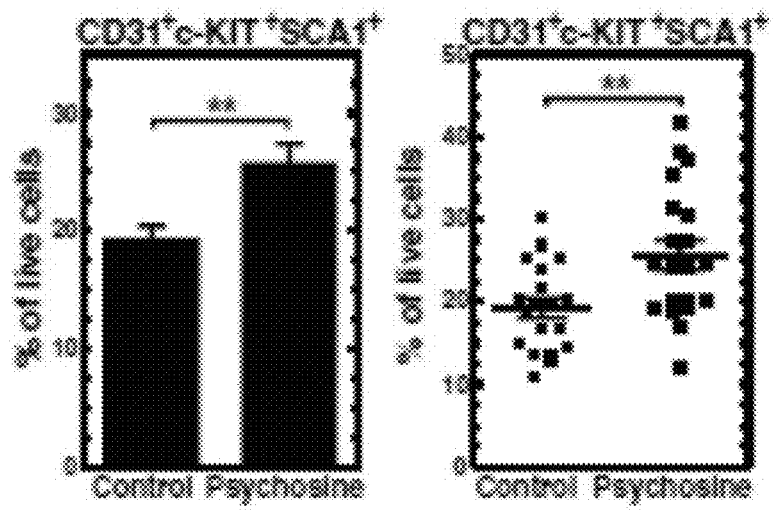

To assess whether Gpr65 activity to suppress hematopoiesis operates in other systems, we used a morpholino (MO) targeting the Gpr65 translation start site (Gpr65_ATG MO) to reduce Gpr65 expression in zebrafish embryos. The Gpr65_ATG MO was injected into 1-cell stage embryos, which were analyzed for expression of the HSC markers Runx1/cmyb using in situ hybridization (ISH) 36 h post-fertilization. The Gpr65_ATG MO dose-dependently increased expression of the HSC markers Runx1/cmyb in the embryos (FIGS. 4F and 4G). A second MO, which blocks Gpr65 splicing (Gpr65_SP MO) yielded an identical result; Gpr65 downregulation induced expression of the HSC markers Runx1/cmyb (FIG. 4G). Thus, GPR65 suppresses hematopoiesis in mouse and zebrafish embryos.

shRNA and morpholino-based loss-of-function strategies may be confounded by off-target effects. As an alternative strategy we used a GPR65 antagonist, the lysosphingolipid galactosylsphingosine (psychosine). Psychosine was initially proposed to be a GPR65 agonist, based on the GPR65 requirement for psychosine-induced multi-nuclear cell formation. Subsequently, it was demonstrated that GPR65 is a proton-sensing receptor, and psychosine antagonizes GPR65. We treated E11.5 AGMs with vehicle or psychosine, and after 96 h, hematopoietic cells were quantitated by flow cytometry. While psychosine did not alter CD31$^+$c-KIT$^+$ cells (FIGS. 5A and 5B), it increased the CD31$^+$c-KIT$^+$SCA1$^+$ cell population, which is known to contain multipotent hematopoietic precursors (FIGS. 5A and 5C). In aggregate, the mouse and zebrafish studies indicate that GPR65 is an endogenous suppressor of hematopoiesis.

Figure 5D:
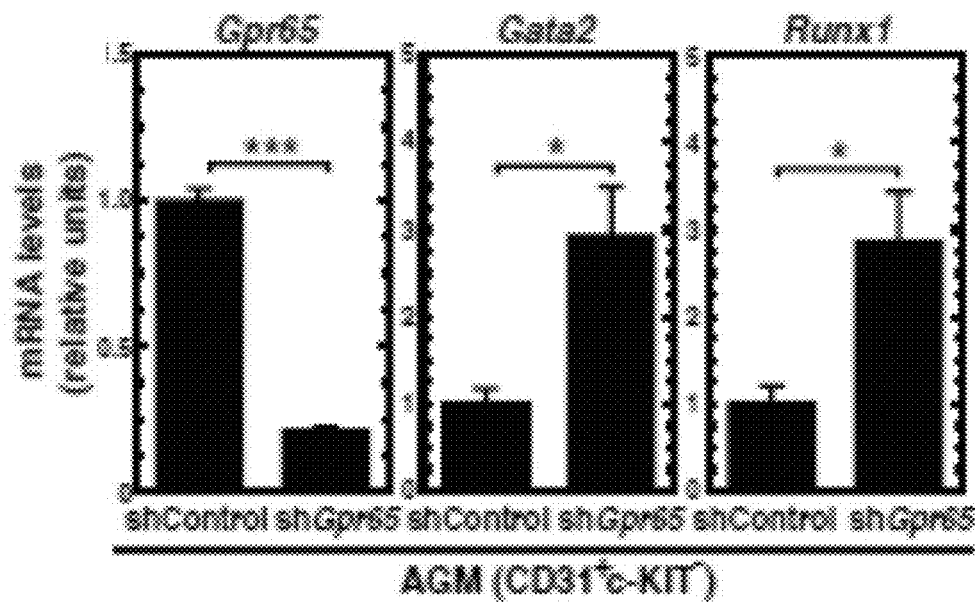
Figure 5E:
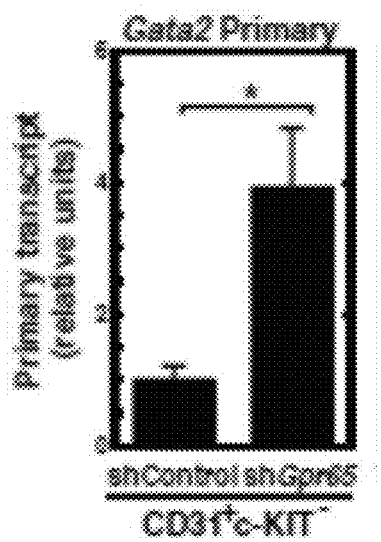

Example 4: GPR65 Establishes Repressive Chromatin and Disrupts an Activating Complex on a Cis-Element Required for Gata2 Transcription To elucidate the mechanism underlying GPR65 suppression of hematopoiesis, we considered whether GPR65 might downregulate key regulators of HSC generation/activity. After knocking down GPR65, we isolated infected CD31$^+$ c-KIT$^-$ endothelial cells that give rise to HSCs. Downregulating Gpr65 mRNA by 60-70% increased Gata2 mRNA 2.9 fold (p=0.03) and its downstream target Runx1 mRNA (p=0.04) 2.9-fold (FIG. 5D). The knockdown elevated Gata2 primary transcripts 3.9-fold (p=0.04) (FIG. 5E), indicating that GPR65 suppresses Gata2 transcription.

To determine whether GPR65 regulates Gata2 expression in zebrafish, we analyzed Gata2 expression using ISH 36 h post-fertilization. Zebrafish has two Gata2 homologs; Gata2b is enriched in hemogenic endothelium and regulates HSPC emergence. Whereas the majority of uninjected embryos exhibited broad staining in the AGM, there was no clear linear zone enriched in hemogenic endothelium. However, Gpr65 ATG MO injected embryos exhibited the linear zone (data not shown), suggesting that GPR65 suppresses Gata2 expression in zebrafish embryos. Given that GATA-2 promotes HSC emergence in the AGM and regulates HSC activity, we propose that GPR65 suppresses hematopoiesis by limiting Gata2 expression and GATA-2 levels.

Figure 6A:
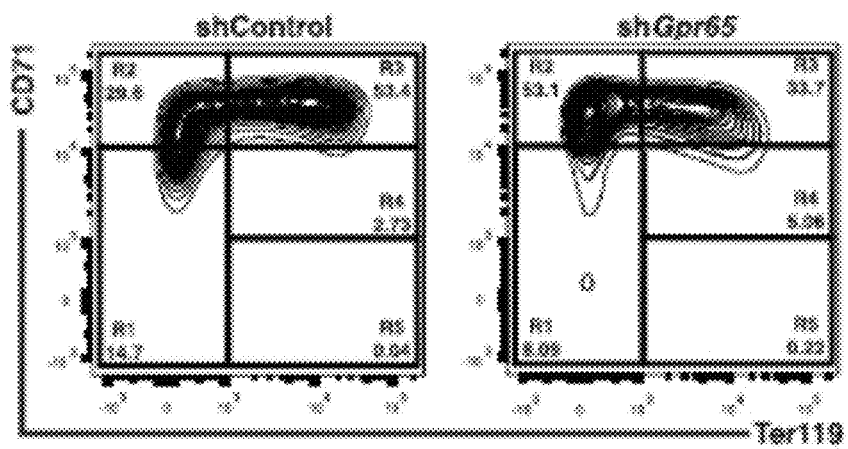
FIGS. 6 A-L show that GPR65 enhances H4K20me1 and limits Scl/TAL1 occupancy at the +9.5 enhancer. (A) Representative flow cytometric plots of erythroid maturation based on expression of CD71 and Ter119 after 3 days of HSPC expansion. The average percentage of total cells in R1 through R5 populations after treatment with control or Gpr65 shRNA is depicted on the right (n=3 independent experiments). (B) RT-PCR analysis of Gpr65 mRNA in fetal liver cells (n=5 independent experiments) (left). Western blot analysis of GPR65 in fetal liver cells (top right) and quantification of the GPR65 and α-tubulin intensities by densitometry (n=8 independent experiments) (bottom right). (C) RT-PCR analysis of Gata2 mRNA and Gata2 primary transcript in total fetal liver cells (n=5 independent experiments). (D) Western blot analysis of GATA-2 in fetal liver cells (top) and quantification of GATA-2/α-tubulin ratio by densitometry (n=6 independent experiments) (bottom). (E) RT-PCR analysis of GATA-2 target gene expression in fetal liver cells (n=5 independent experiments). (F, G, H, and I) Real-time RT-PCR analysis of Gpr65 mRNA (F), Gata2 mRNA (G), Gata2 primary transcript (G) and GATA-2 target genes in FACS-sorted R2 cells (n=3 independent experiments) (I). Western blot analysis of GATA-2 in FACS-sorted R2 cells and quantification of the intensities of the GATA-2 to α-tubulin band by densitometric analysis (n=4 independent experiments) (H). (J) Strategy in which fetal liver HSPCs were isolated from E14.5 embryos heterozygous for the +9.5 site at Gata2. Cells were infected with Control or shGpr65 and cultured under expansion conditions for 3 days (left). Allele-specific real-time RT-PCR analysis of Gata2 transcripts from the WT and mutant +9.5 alleles in total fetal liver cells (n=3 independent experiments) (middle) and FACS-sorted R2 cells (n=3 independent experiments) (right). (K) RT-PCR analysis of Setd8 mRNA in fetal liver cells treated with control or Gpr65 shRNA (n=5 independent experiments) (top left). H4K20me1, GATA-1 and Scl/TAL1 chromatin occupancy measured by quantitative ChIP at the +9.5 site in fetal liver cells cultured under expansion medium and treated with control or Gpr65 shRNA (H4K20me1: n=8 independent experiments; GATA-1: n=4 independent experiments; Scl/TAL1: n=6 independent experiments) (right). H4K20me1 levels at the repressed MyoD promoter and at the active Eif3k promoter serve as controls (middle left). Scl/TAL1 chromatin occupancy at 114 kb upstream from the c-Kit promoter and Lyl1 exon1 as controls (bottom left). The dashed line illustrates the highest value obtained with PI antibody. (L) Model: GATA-2, a positive regulator of hematopoiesis, upregulates Gpr65, which encodes a negative regulator of hematopoiesis, to control HSC emergence. GPR65 represses Gata2 expression by increasing H4K20me1, a repressive chromatin mark, which in turn restricts +9.5 occupancy by the activator Scl/TAL1. Error bars represent SEM. *, $P<0.05$;, $P<0.01$; *, $P<0.001$ (two-tailed unpaired Student's t-test).
Figure 6A:
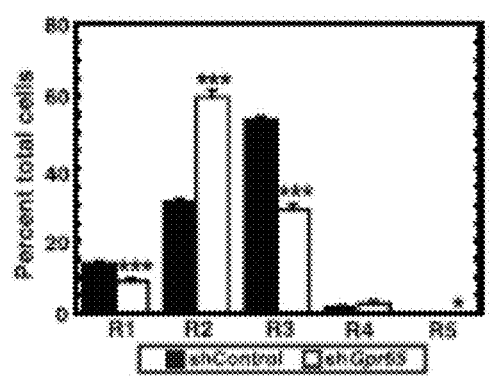
Figure 6B:
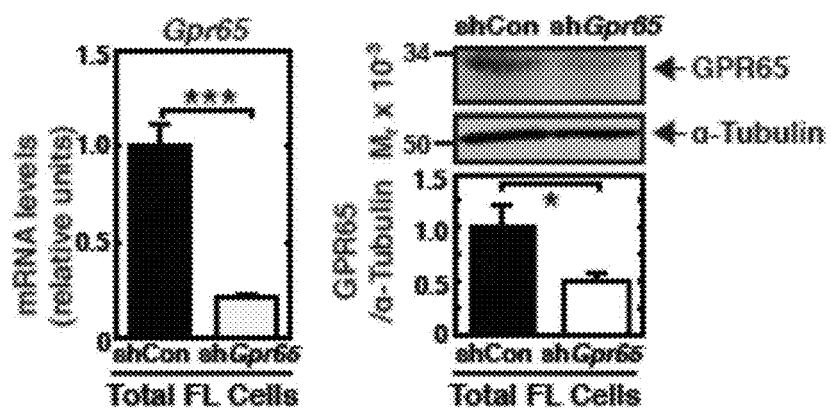
Figure 6C:
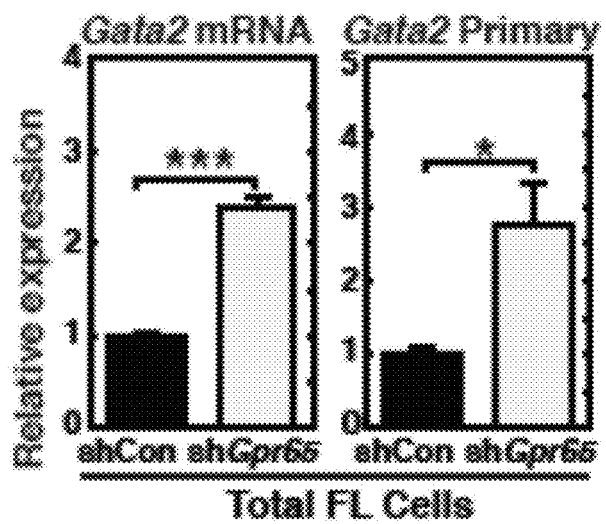
Figure 6D:
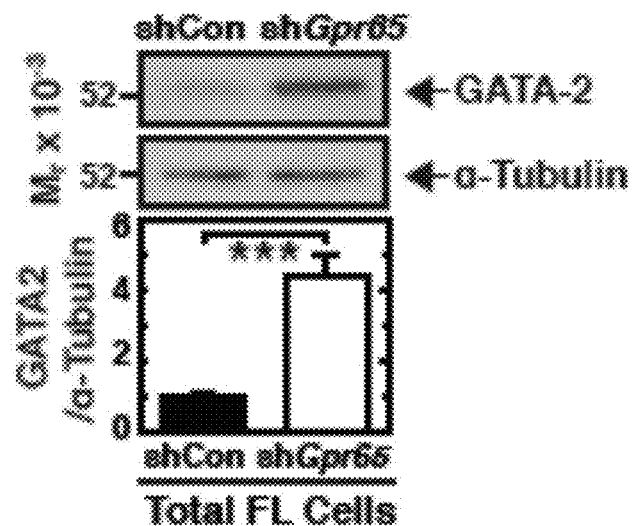
Figure 6E:
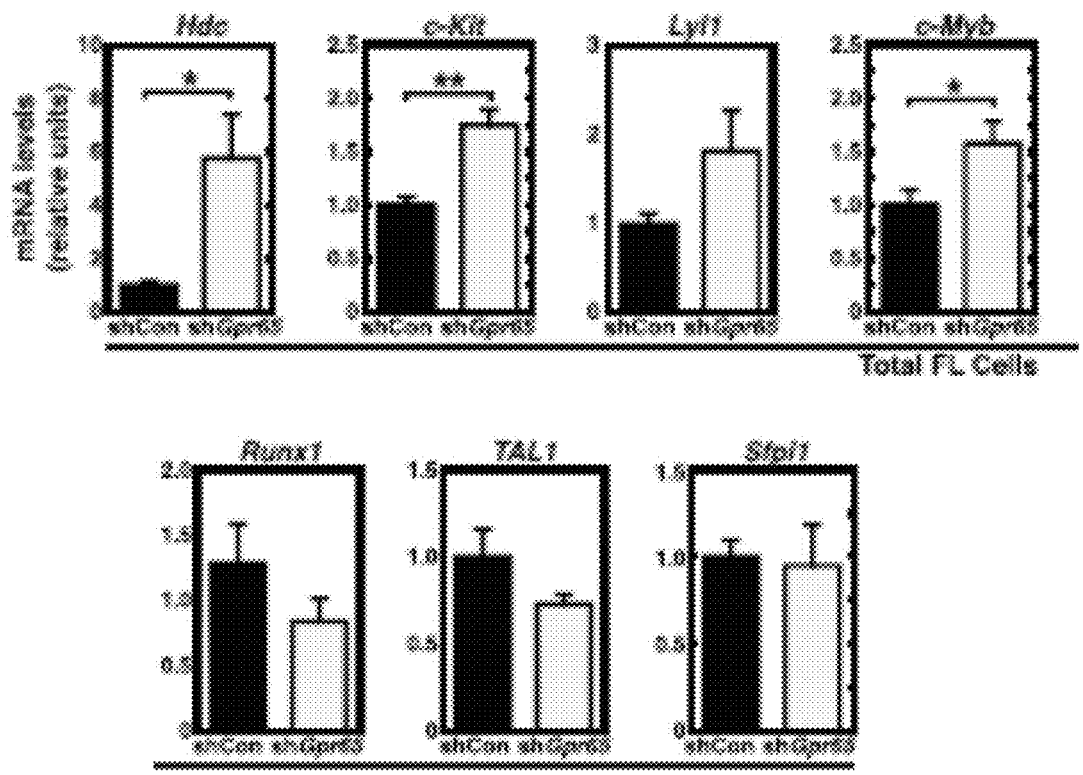
Figure 6F:
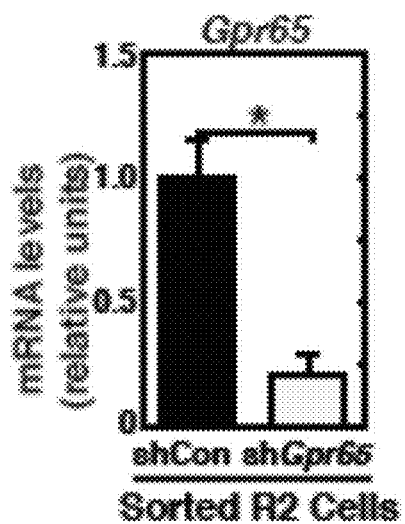
Figure 6G:
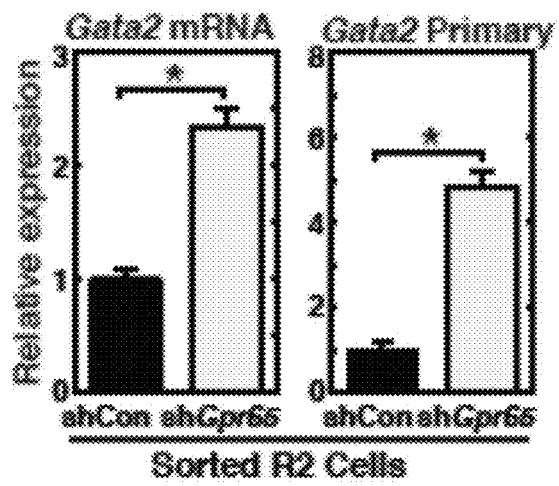
Figure 6H:
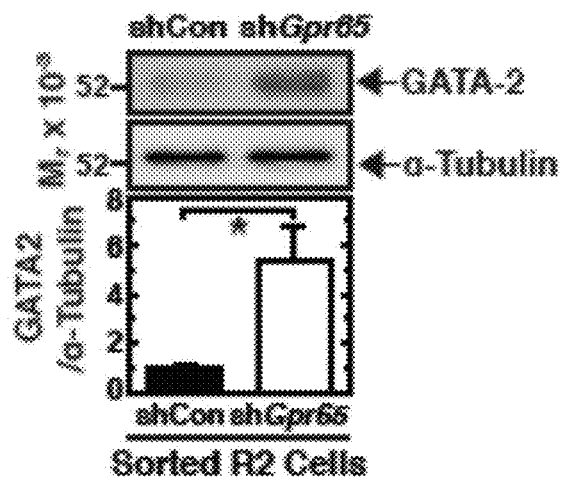
Figure 6I:
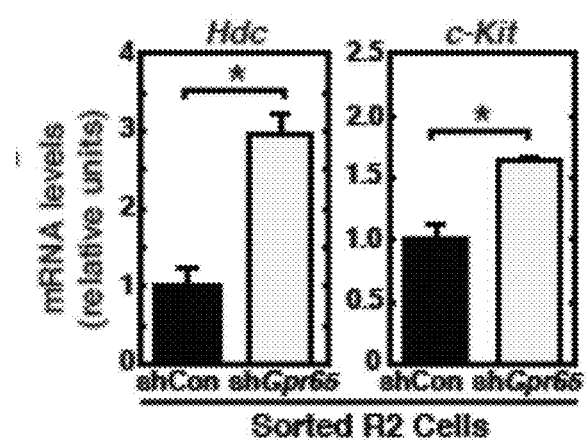

As Gpr65 is expressed in AGM endothelium and HSPCs, we asked whether GPR65 represses Gata2 expression in other contexts. Fetal liver hematopoietic precursors express Gata2, and as GATA-1 rises upon erythroid maturation, Gata2 is repressed. We isolated Lin hematopoietic precursors from E14.5 fetal livers and tested whether reducing Gpr65 expression with the Gpr65 shRNA retrovirus alters Gata2 expression. Cells were expanded for 72 h to increase HSPCs, while suppressing differentiation. Downregulating Gpr65 increased the proerythroblast-enriched R2 population 1.9-fold (p=0.0002) and reduced the R3 population (early and late basophilic erythroblasts) 1.6-fold (p=0.0003) (FIG. 6A). Increased R2 cells, concomitant with reduced R3 cells, suggests that GPR65 promotes erythroid maturation. Downregulating Gpr65 mRNA by 70-80%, which lowered GPR65 protein by 50%, increased Gata2 mRNA and primary transcripts 2.4 (p=3.65E-06) and 2.8 fold (p=0.014), respectively (FIGS. 6B and 6C). Western blot analysis of fetal liver cells revealed that reducing GPR65 expression upregulated GATA-2 (FIG. 6D). Increased GATA-2 selectively elevated GATA-2 target gene expression (FIG. 6E). To test whether increased Gata2 expression reflected a change in cellularity, we used FACS to isolate the GATA-2-expressing R2 population and compared gene expression in control and knockdown R2 cells. Gpr65 knockdown upregulated Gata2 mRNA 2.3 fold (p=0.02), primary transcript 4.8 fold (p=0.01), GATA-2 protein, and GATA-2 target genes in FACS-sorted R2 cells (FIGS. 6F, 6G, 6H and 6I). These results indicate that GPR65 represses Gata2 in the AGM and fetal liver. Since GATA-1 needs to repress Gata2 transcription early in erythroid maturation, upregulated Gata2 expression caused by the Gpr65 knockdown would be expected to increase immature R2 cells as observed (FIG. 6A).

Figure 6J:
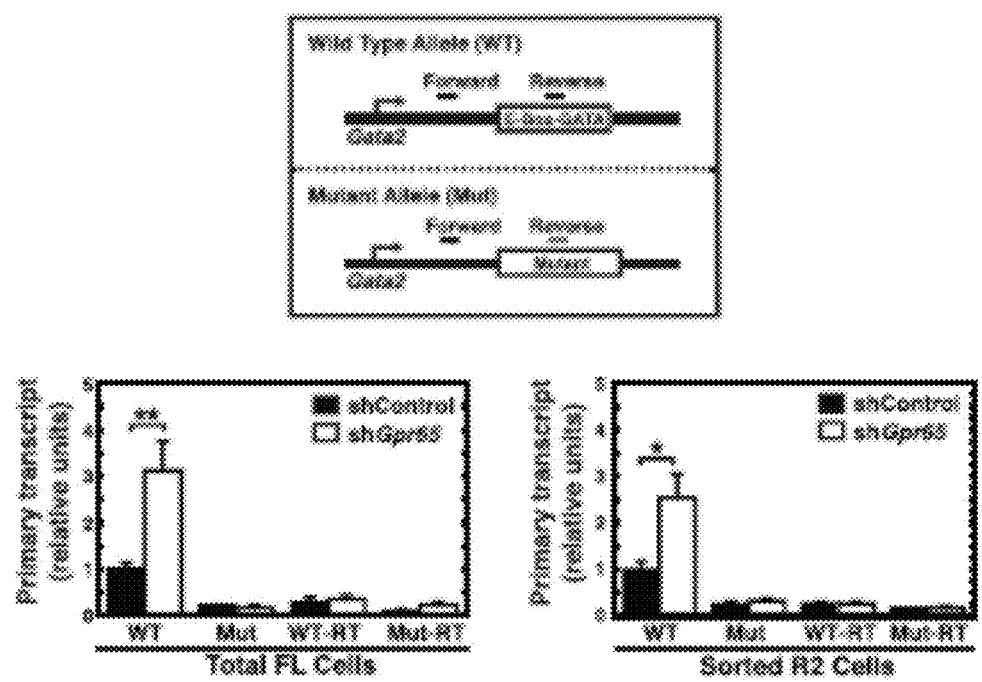

The +9.5 enhances Gata2 expression in the AGM and fetal liver. Deleting the +9.5 abrogated HSC generation in the AGM and disrupted establishment of the HSPC compartment in the fetal liver. To determine if increased Gata2 transcription upon Gpr65 knockdown requires the +9.5, we isolated Lin HSPCs from E14.5 +9.5$^{+/-}$ fetal livers and infected cells with Gpr65 shRNA retrovirus. After 72 h of expansion culture, allele-specific primers were used to quantitate primary transcripts from wild type (WT) and mutant (Mut) 9.5 alleles in fetal liver cells and FACS-purified R2 cells (FIG. 6J). Gpr65 knockdown upregulated Gata2 primary transcripts from the wild type, but not the +9.5 mutant, allele (FIG. 6J), demonstrating importance of the +9.5 for Gata2 transcription.

Figure 6K:
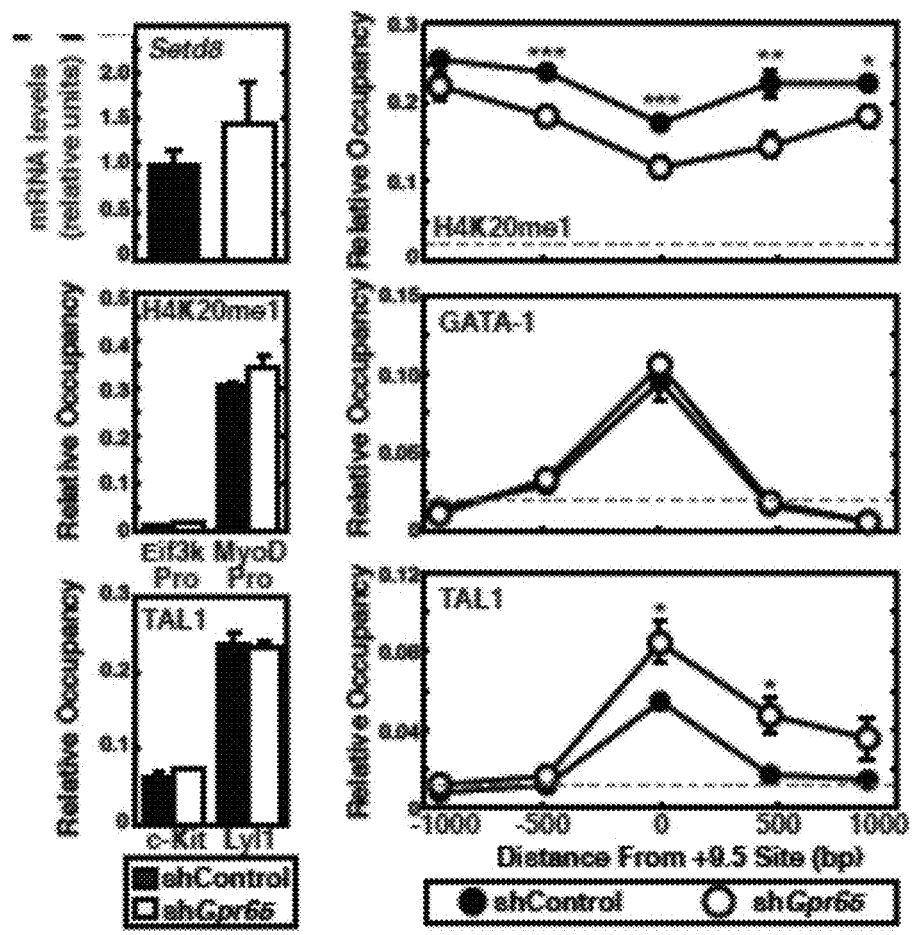
Figure 6L:
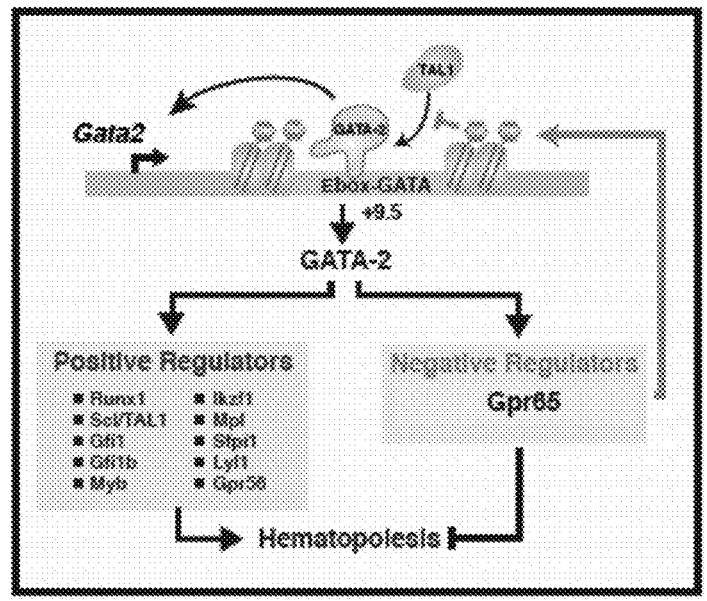

Previously, we demonstrated that SetD8, the enzyme that monomethylates H4K20, represses Gata2 expression via the +9.5 site. We tested the relevance of this mechanism to GPR65-mediated Gata2 repression. We conducted quantitative chromatin immunoprecipitation (ChIP) analysis for H4K20me1 in fetal liver cells (control or Gpr65 knockdown) after culturing for 72 h. Downregulating Gpr65 did not alter the SetD8 mRNA level (FIG. 6K). Gpr65 downregulation reduced H4K20me1 at the +9.5 site (p=0.002) and at sites 480 bp upstream (p=0.002), 466 bp downstream (p=0.006), and 880 bp downstream (p=0.02) of the +9.5 site (FIG. 6K). H4K20me1 was unaltered at the repressed muscle-specific MyoD promoter and the constitutively active Eif3k promoter. These results support a mechanism in which GPR65 represses Gata2 by increasing a repressive chromatin mark at the +9.5 site. The basic helix-loop-helix transcription factor Scl/TAL activates Gata2 transcription through the +9.5 site, and Scl1/TAL1 chromatin occupancy is reduced at the +9.5 site during GATA-1-mediated Gata2 repression. As Gpr65 downregulation decreased H4K20me1 at the +9.5 site, this alteration may generate chromatin that is more accessible to cognate binding factors. To determine if GPR65 alters GATA-1 and Scl/TAL1 occupancy, we quantitated GATA-1 and Scl/TAL1 occupancy at the +9.5 site in fetal liver cells infected with control shRNA or Gpr65 shRNA-expressing retrovirus. While knocking down Gpr65 did not alter GATA-1 occupancy at the +9.5, the knockdown increased Scl/TAL1 occupancy at the +9.5 1.6-fold (p=0.02) but not at other target loci (Lyl1 and Kit) (FIG. 6K and data not shown). These results suggest that GPR65 represses Gata2 by establishing repressive chromatin that limits Scl/TAL1 occupancy at the +9.5 site (FIG. 6L).

Example 5: Psychosine Regulates Gata2 Expression

Figure 7A:
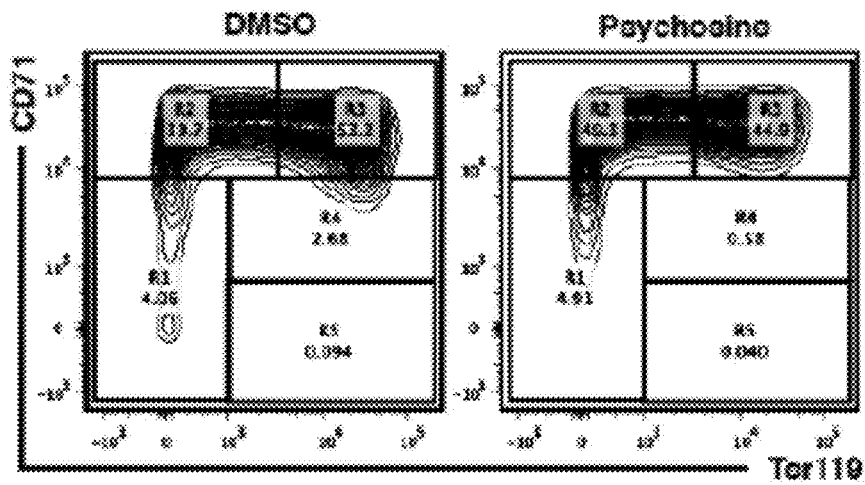
FIG. 7 A-D show that psychosine increased Gata2 expression and slightly blocks erythroipoiesis. (A) Representative flow cytometric plots of erythroid maturation based on CD71 and Ter119 expression 3 days after HSPC expansion (left). The average percentage of cells in R1 through R5 populations after treatment with control (DMSO) or psychosine (right). (B) RT-PCR analysis of Gata2 mRNA and Gata2 primary transcript in total fetal liver cells. (C) RT-PCR analysis of Gata2 mRNA and Gata2 primary transcript in FACS-sorted R2 cells. (D) Western blot of GATA-2 and α-Tubulin in FACS-sorted R2 cells. Error bars represent SEM. *$P<0.05$; **$P<0.01$ (two-tailed unpaired Student's t test)
Figure 7A:
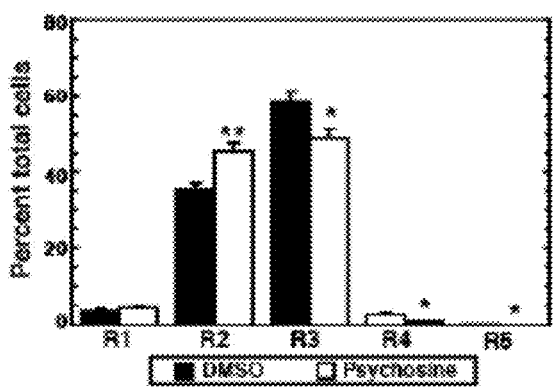
Figure 7B:
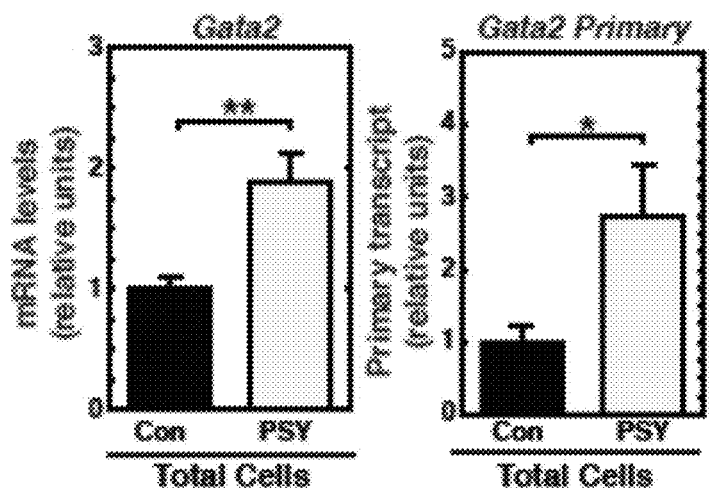
Figure 7C:
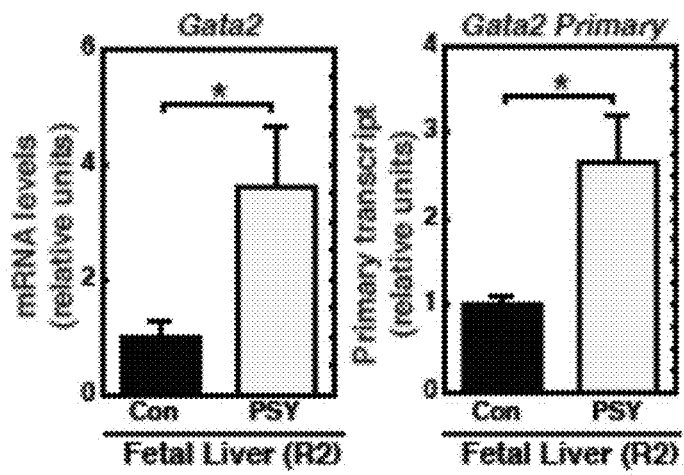
Figure 7D:
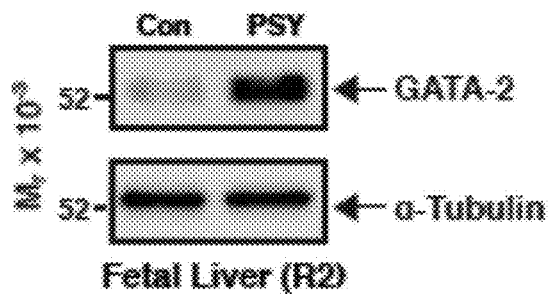

To test whether psychosine regulates Gata2 expression, we isolated Lin$^-$ hematopoietic precursors from E14.5 fetal livers and treated cells with psychosine. After 72 h of ex vivo culture, flow cytometry was used to quantitate erythroid maturation. This analysis revealed that treatment with psychosine dissolved in DMSO slightly, but consistently, increased R2 cells and decreased R3 cells in comparison to cells treated with DMSO alone (control) (FIG. 7A). suggesting that psychosine has some capacity to inhibit erythroid maturation. RNA analysis revealed that Gata2 mRNA and primary transcript levels were 2-3 fold higher in the fetal liver cells treated with psychosine versus the DMSO-treated control cells (FIG. 7B), indicating that psychosine increases Gata2 expression in fetal liver cells. To test whether increased Gata2 expression reflected a change in cellularity or increased Gata2 transcription independent of potential cellular changes, fluorescence activated cell sorting (FACS) was used to isolate the GATA-2-expressing R2 population. We compared Gata2 expression in control and psychosine-treated, isolated R2 cells. RT-PCR and Western blot analysis revealed that psychosine increased Gata2 mRNA, Gata2 primary transcript (unprocessed mRNA that serves as a metric of transcription), and GATA-2 protein in R2 cells (FIGS. 7C and 7D).

Example 6: Activity of Psychosine Derivatives

Figure 8:
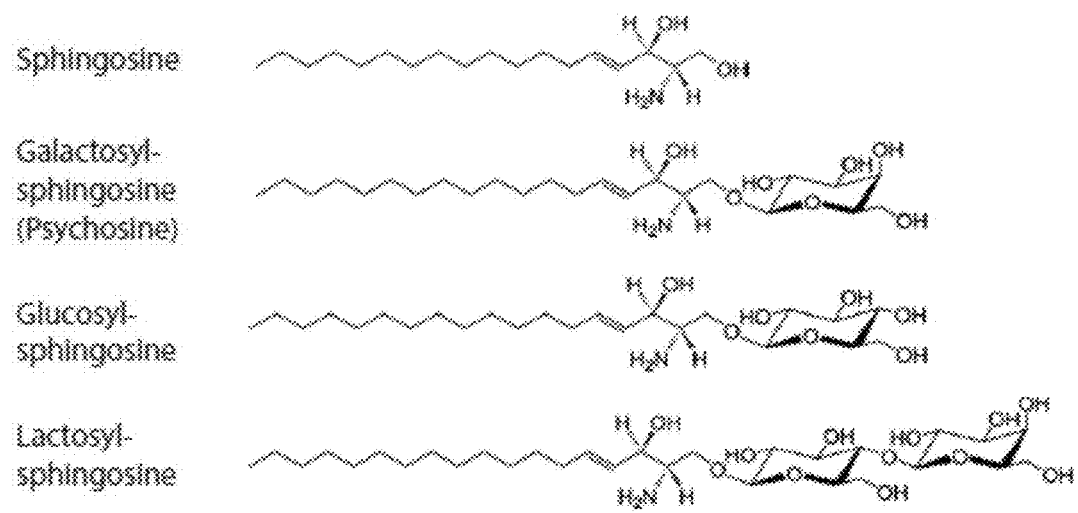
FIG. 8 shows the structure of sphingosine, galactosylsphingosine (psychosine), glucosylsphingosine, and lactosylsphingosine.
Figure 9A:
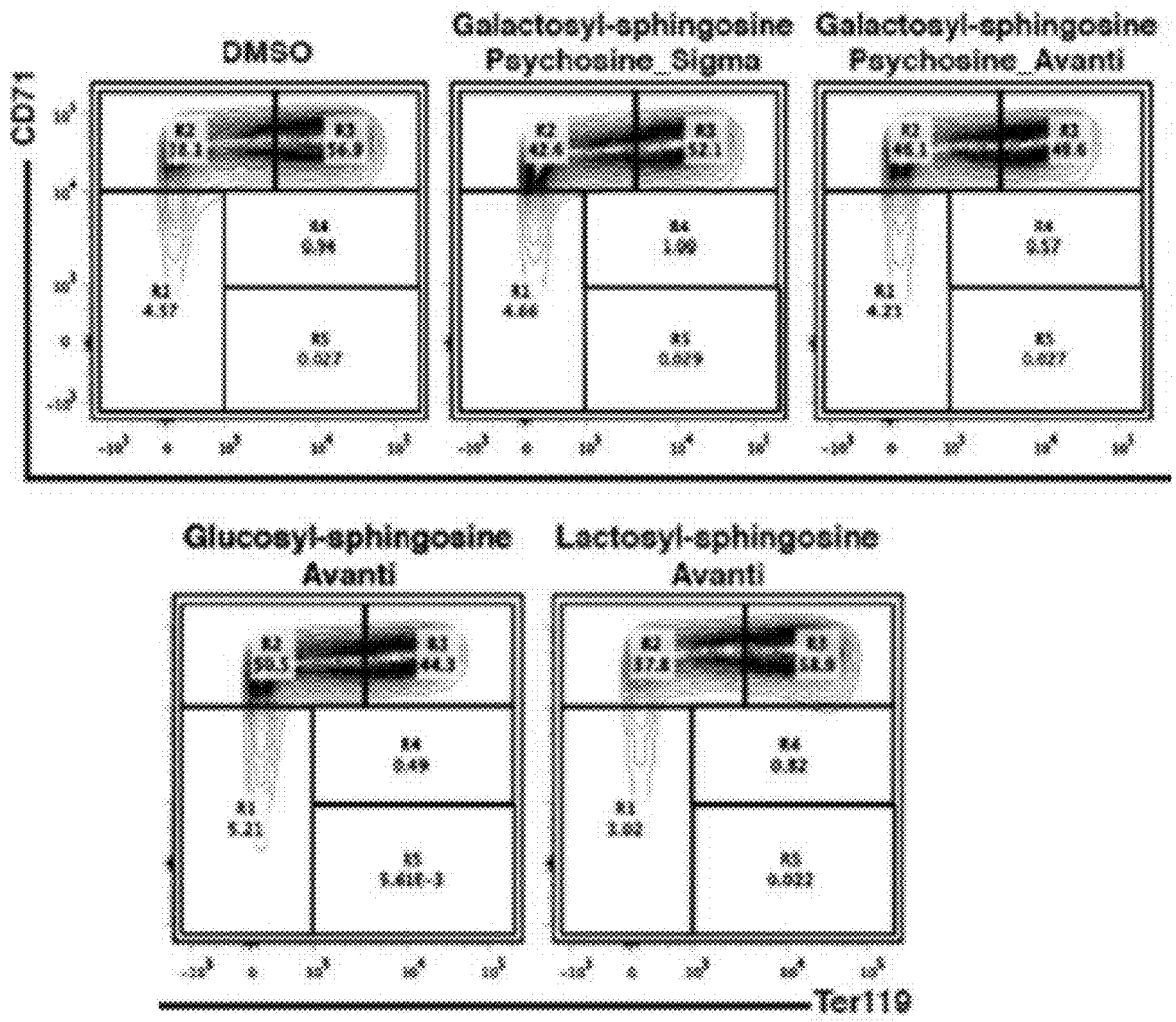
FIG. 9 A-D show that glucosylsphingosine, but not lactosylsphingosine showed similar activity as psychosine. (A) Representative flow cytometric plots of erythroid maturation based on CD71 and Ter119 expression 3 days after HSPC expansion. (B) The average percentage of cells in R1 through R5 populations after infection with psychosine (GalSph), glucosylsphingosine (GluSph), or lactosylsphingosine (LacSph). (C) RT-PCR analysis of Gata2 mRNA in fetal liver cells. (D) Western blot analysis of GATA-2 in fetal liver cells (left), and quantification of GATA-2 and tubulin intensities by densitometry (right). Error bars represent SEM. *$P<0.05$; $P<0.01$; *$P<0.001$ (two-tailed unpaired Student's t test)
Figure 9B:
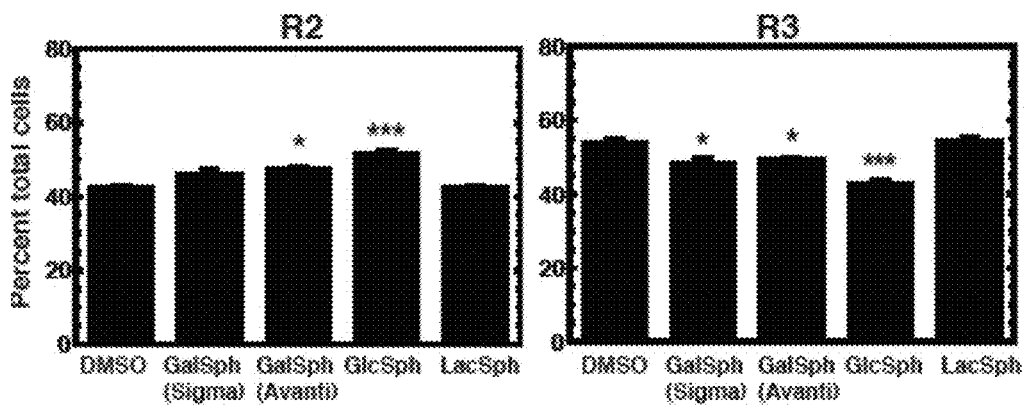
Figure 9C:
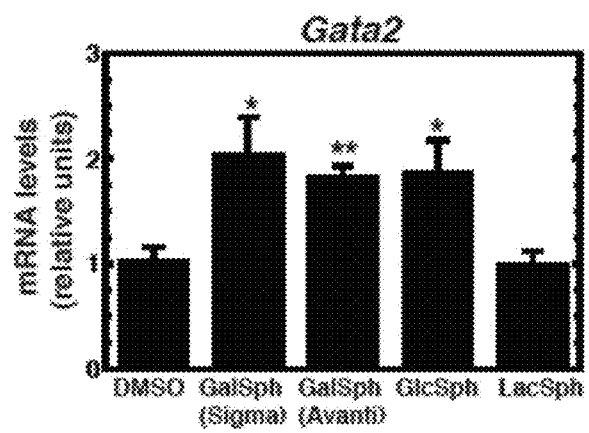
Figure 9D:
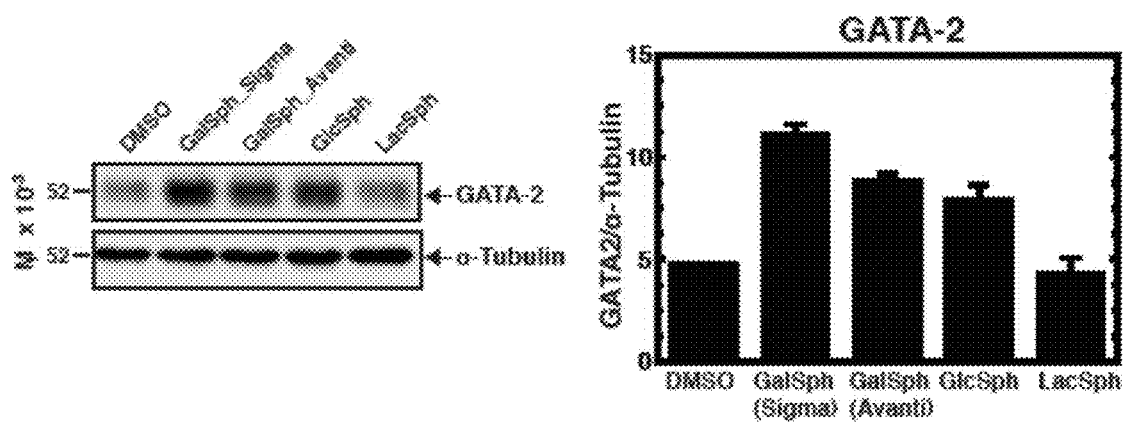

Furthermore, we analyzed the activity of structurally distinct derivatives of psychosine (glucosylsphingosine and Lactosylsphingosine), specifically, the role of the sugar constituent in the fetal liver (FIG. 8). To determine the activity of psychosine derivatives, we treated the Lin- HSPCs with DMSO as control, psychosine from Sigma or Avanti, glucosphingosine and lactosphingosine. Flow analysis revealed that glucosylsphingosine, but not lactosylsphingosine exhibited similar activity as psychosine, which slightly but significantly blocks erythropoiesis (FIGS. 9A and 9B). RNA and protein analysis showed that glucosylsphingosine has similar activity with psychosine, that upregulated Gata2 expression at RNA and protein level (FIGS. 9C and 9D).

Example 7: Aorta, Gonad, Mesonephros (AGM) Culture and Transplant Assay

AGM explant culture. E11.5 AGMs are dissected and cultured by methods known in the art. In brief, intact AGMs are cultured for 4 d on Durapore filters (Millipore) at the air-liquid interface in IMDM+ Media (Iscove's modified Dulbecco's media [IMDM; Invitrogen] supplemented with 20% FBS [Gemini], 4 mM 1-glutamine [Invitrogen], 1% penicillin/streptomycin [Invitrogen], 0.1 mM mercaptoethanol, 100 ng/ml IL-3 [R&D Systems], 100 ng/ml Flt3L [R&D Systems], and 1.5% conditioned medium from a kit ligand-producing CHO cell line).

AGM reaggregate culture. AGMs are dissociated and reaggregated for culturing by methods known in the art. A single-cell suspension of AGM cells is drawn into a 200-µl pipette tip. The tip containing the cell suspension is blocked with Parafilm and centrifuged in a 15-ml centrifuge tube at 300 g for 5 min. After removing the Parafilm, the reaggregate is extruded onto the Durapore filter and cultured at the air-liquid interface in IMDM+ media for 4 d. AGM reaggregates, as well as whole AGM explants, are cultured in a humidified incubator at 37° C. with 5% carbon dioxide.

Uncultured AGMs and cultured AGM explants/reaggregates are digested in 0.1% collagenase in PBS containing 10% FBS at 37° C. for 30 min and then dissociated by passing through a 27-G needle. Dissociated AGM cells were subjected to colony assay, transplantation assay, flow cytometry, and cell sorting.

Transplantation assay. Adult C57BL/6 recipient mice (CD45.1+; 6-8 wk old) are lethally irradiated with 2 doses of 500 rad each from a Cesium source. Dissociated cells from E11.5 cultured CD45.2+ AGM explants are combined based on their genotypes. 50,000 nucleated AGM cells were co-injected into individual irradiated CD45.1+ recipient mice with 200,000 CD45.1+ spleen cells as a support and 20,000 CD45.1+ bone marrow cells. The transplanted recipient mice are maintained on trimethoprim/sulfamethoxazole-treated water for 2 wk. Blood is obtained from the retroorbital venous sinus regularly after transplantation for flow cytometric analysis, as known in the art. Directly conjugated antibodies specific for the following surface antigens are purchased from eBioscience: CD19 (eBioID3), CD45.1 (A20), CD45.2 (104), Mac-1 (M1/70), and Thy1.2 (53-2.1).

Discussion

Genetic networks orchestrating stem and progenitor cell transitions can be deconstructed into regulatory modules termed network motifs. Whereas considerable progress has been made to identify individual gene constituents of genetic networks controlling hematopoiesis, many questions remain unanswered regarding how the numerous genes involved form network motifs, how the network motifs amalgamate into the intact circuitry, and whether the circuitry has an inherent plasticity and undergoes remodeling in states of altered hematopoiesis such as stress, aging, and malignancy.

Since the GATA-2-dependent genetic network promotes hematopoiesis, it seems reasonable to infer that GATA-2-induced factors are positive mediators of key steps in this process, including EHT, HSPC self-renewal, and HSPC differentiation. In erythroid cells, GATA-1 activates heme biosynthetic genes, globin subunits, and constituents of the red cell cytoskeleton, all required for erythroid maturation. Moreover, GATA-1 represses Gata2, Lyl1, and Kit, as a means of enabling erythroid maturation. GATA-2 activates Kit, an essential regulator of HSPCs, consistent with GATA-2 promoting HSPC development and function.

Using a coupled bioinformatics-experimental strategy, we analyzed the large GPCR gene family, with the goal to discover GATA-2-induced GPCRs that promote HSPC transitions. This analysis led to the surprising finding that GATA-2 activates Gpr65 expression, which in turn suppresses hematopoiesis via negative feedback on the Gata2 gene. This negative feedback mechanism conforms to a type I incoherent feed-forward loop, which is defined as an input (GATA-2) that elicits an output (EHT or hematopoiesis) through positive (increased Gpr65 expression) and negative (GPR65 suppression of hematopoiesis) paths. Type I incoherent feed-forward loops shape the dynamics of the respective mechanism, with the existing paradigm assuming that the feed-forward loop confers a pulse of activity to accelerate the reaction. Since the regulatory constituents and associated network motifs governing HSPC transitions are still being identified, the dynamics of specific steps in these transitions are largely unexplored. The mechanism of GPR65-mediated Gata2 repression involved elevation of a repressive histone mark, H4K20me1, associated with reduced occupancy by the activator Scl/TAL1. In principle, GPR65 might directly target chromatin to restrict Scl/TAL1 occupancy or might reduce Scl/TAL1 occupancy prior to chromatin modification. Regardless of the order-of-events in this mechanism, the analysis provided herein established a GATA factor-GPCR-dependent type I incoherent feed-forward loop that suppresses, rather than promotes hematopoiesis.

Gpr65, originally identified as T-cell Death-Associated Gene-8 (Tdag8), is a proton/acid-activated GPCR. Whereas GPR65 had not been linked to the control of HSPC transitions, it was reported to be a pro-apoptotic factor in glucocorticoid-induced lymphocyte apoptosis and to regulate cytokine production from macrophages. However, targeted deletion of Gpr65 revealed it was dispensable for glucocorticoid-induced thymocyte apoptosis in vivo and in vitro. These results were suggested to reflect redundancy with related pH-sensing GPCRs, including G2A, OGR1, and GPR4, which would create a formidable obstacle to dissect Gpr65 function in vivo. Although the impact of the pH-sensing mechanism to GATA-2 function in the AGM and fetal liver is unclear, the endogenous GPR65 antagonist psychosine resembled Gpr65 shRNA in upregulating Gata2 expression and hematopoiesis.

As GPR65 suppressed HSPC generation from primary mouse AGM explants, it is instructive to consider potential consequences of ablating this mechanism in vivo. Abrogation of the mechanism would upregulate HSPC generation, which might expand the hematopoietic compartment. However, given the capacity of HSPCs to compensate for hematopoietic perturbations in certain contexts, HSPC upregulation might be normalized to ensure physiological homeostasis. Nevertheless, since ablating Gpr65 would be expected to increase, rather than decrease HSPCs, evaluating the role of the GATA-2-GPR65 circuit in vivo will require a careful quantitative analysis of HSPCs. Theoretical considerations of type I incoherent feed-forward loops would suggest an alteration of the dynamics of specific steps of hematopoiesis, which might not be evident from steady-state analyses. It is attractive to propose that this suppressive mechanism is particularly important when the demand for hematopoiesis increases, e.g. during stress, since an unopposed increase could yield deleterious blood cell elevations.

In summary, the present inventors have discovered that GATA-2 activity to promote hematopoiesis involves induction of both positive and negative mediators, the balance of which establishes the physiological output. Based on the GPR65 pH-sensing function, one can develop technologies to analyze the pH microenvironment of the AGM and other anatomical sites of hematopoiesis and to establish the role of GPR65 as an endogenous mediator of pH-dependent, dynamic alterations in HSPC transitions.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of expanding a population of hematopoietic stem cells, comprising
contacting the population of hematopoietic stem cells with an effective amount of an inhibitor of G-protein coupled receptor 65 (GPR65), and
culturing the cells to provide a population of expanded, substantially undifferentiated hematopoietic stem cells, wherein the inhibitor of G-protein coupled receptor 65 (GPR65) is an inhibitory nucleic acid molecule.

2. The method of claim 1, wherein the method is performed ex vivo.

3. The method of claim 1, wherein the population of hematopoietic stem cells is obtained from a mammalian tissue selected from umbilical cord blood, peripheral blood, or bone marrow.

4. The method of claim 1, wherein the population of hematopoietic stem cells is obtained from mammalian umbilical cord blood.

5. The method of claim 1, wherein the population of hematopoietic stem cells are of human origin.

6. The method of claim 1, wherein the inhibitory nucleic acid molecule is a small interfering RNA, an antisense RNA, a ribozyme, or a triple helix nucleic acid.

7. The method of claim 6, wherein the small interfering RNA is an siRNA or an shRNA.

8. The method of claim 7, wherein the small interfering RNA comprises 19 to 29 nucleotides that are substantially complementary to a sequence of SEQ ID NO: 1.

9. The method of claim 8, wherein the small interfering RNA is an shRNA having SEQ ID NO: 2 or SEQ ID NO: 3.

10. A method for administering an expanded population of hematopoietic stem cells to a patient in need thereof, comprising
culturing a population of hematopoietic stem cells in a hematopoietic stem cell expansion medium ex vivo for a period of time sufficient to provide an expanded population of hematopoietic stem cells, wherein the hematopoietic stem cell expansion medium comprises an inhibitor of G-protein coupled receptor 65 (GPR65), and
administering the expanded population of hematopoietic stem cells to the patient,
wherein the inhibitor of G-protein coupled receptor 65 (GPR65) is an inhibitory nucleic acid molecule.

11. The method of claim 10, wherein the population of hematopoietic stem cells is obtained from a mammalian tissue selected from umbilical cord blood, peripheral blood, or bone marrow.

12. The method of claim 10, wherein the population of hematopoietic stem cells is obtained from mammalian umbilical cord blood.

13. The method of claim 12, wherein the hematopoietic stem cells are human hematopoietic stem cells and the patient is a human patient.

14. The method of claim 13, wherein the inhibitory nucleic acid molecule is a small interfering RNA, an antisense RNA, a ribozyme, or a triple helix nucleic acid.

15. The method of claim 14, wherein the small interfering RNA is an siRNA or an shRNA.

16. The method of claim 15, wherein the small interfering RNA comprises 19 to 29 nucleotides that are substantially complementary to a sequence of SEQ ID NO: 1.

17. The method of claim 16, wherein the patient is in need of treatment for leukemia, multiple myeloma, lymphoma, graft versus host disease, aplastic anemia, sickle cell anemia, Severe Combined Immune Deficiency (SCID), Wiskott-Aldrich Syndrome (WAS), IPEX Syndrome, Hemophagocytic Lymphohistiocytosis (HLH), X-linked Lymphoproliferative Disease (XLP) or Chronic Granulomatous Disease (CGD).

* * * * *

SEQUENCE LISTING

<160> NUMBER OF SEQ ID NOS: 45

<210> SEQ ID NO 1
<211> LENGTH: 2153
<212> TYPE: DNA
<213> ORGANISM: Mus musculus

<400> SEQUENCE: 1

```
aacactgctg gtttctcttc ttgatacaag cagatttgcc agcctcctca gtcaagagaa      60
gcatccctcc agaaacaggg aaacatgaca cttttgaaag aatgccaaac ggcgtgaaaa     120
taaaaacaga gcattcccat ttgcaccgac caatctccaa tctcctgtaa gattcaaaag     180
ggcaagcaag aggcggtgac cgttcacgaa agctaaaatc ccatgctatt gaacatgaag     240
acttctgatg cttaaatctc attaactgct ttaagtcact cccaggagct tggatcccaa     300
cttctagcag taatagtctg tgtaaaaaaa aaaaaaaaat cagtctacaa ccactctcta     360
aatgcatgga tgaactcatc agaacatcaa aacccaagga aaccctaaga gagaagaatt     420
ctaataaaaa gaattttaca ttgaaaactt acaaggcaag gtcccttcc ctgctgacag      480 cctaagaagt gatgtaactg ccactgtgaa gaccatggcg atgaacagca tgtgcattga     540
agagcagcgc cacctcgaac actatttgtt cccggtggtc tacataattg tgtttatagt     600
cagcgtccca gccaacatcg gatctttatg cgtatccttt ctgcaagcga agaaggaaaa     660
tgagctaggg atttacctct tcagtctgtc cctgtcagac ctgctgtatg cgctgactct     720 gccctctgg atcaattaca cttggaataa agacaactgg actttctctc ccaccttgtg      780
caaaggaagc gttttcttca cctacatgaa cttttacagc agcacggcgt tcctcacttg     840
cattgccctg gaccgctatt tagcagtcgt ctaccctctg aagttttcct tcctaagaac     900
gagaagattc gcgtttatta ccagcctctc catctggata ttagagtcct tctttaactc     960
tatgcttctg tggaaagatg aaacgagtgt tgaatattgt gactcggaca aatctaattt    1020
cactctctgc tatgacaaat accctctgga gaaatggcag ataaacctca acctgtttcg    1080
gacgtgcatg ggctacgcaa tacccttgat caccatcatg atctgcaacc ataaagtcta    1140
ccgagctgtg cggcacaacc aagccacgga aaacagcgag aagagaagga tcataaagtt    1200
gcttgctagc atcacgttga ctttcgtcct atgctttacc cccttccacg tgatggtgct    1260
catccgctgc gttttagagc gcgacatgaa cgtcaatgac aagtctggat ggcagacgtt    1320
tacggtgtac agagtcacag tagccctgac gagtctaaac tgtgttgccg atcccattct    1380
gtactgcttt gtgactgaga cggggagagc tgatatgtgg aacatattaa aattgtgtac    1440
taggaaacac aatagacacc aagggaaaaa aagggacata cttctgtgt ccacaagaga     1500 tgctgtagaa ttagagatta tagactaaga ggtggaggca ggttaagtta catggtatta    1560
```

```
tttaatgaaa cttacatttt ggaaaagaaa tctggcatag tagaacccag tggaaatagt    1620
ttgaaggtac attgtatgac tcctatgttg gctttattaa gtaaggtata gaaatgtatt    1680
atcttgtatg tattctaatg actaggcatc attgttttag taccaattct ctttgcctct    1740
atgttataac ccctaagaag cacgcgggac tgttcgtctt taaatcagtg gccattctat    1800
ctgactacta tgacttttttg ttgttgttct gctttgggtt ttcagtctgc ctgcatcagt    1860
cttctcctct gtatacgtct gtcttcaaca aatgtaagga ctaaataccc ctcccgatca    1920
catccattat caaggatttg aagccactcc atgtactggg ttataaaaga aatgttctca    1980
tgaactttca tgaagtttac atacctttgg ggatctagtc accgagtcac ataaagtaaa    2040
agtaaatgga ttttgtattt tggtcttgat ttctttatat ttatagctga atatgtttat    2100
atggatgagt ttccgtccag acagataaat atttatgggc aatcttaaaa aaa           2153

<210> SEQ ID NO 2
<211> LENGTH: 97
<212> TYPE: DNA
<213> ORGANISM: Artificial Sequence
<220> FEATURE:
<223> OTHER INFORMATION: snRNA sequence

<400> SEQUENCE: 2
tgctgttgac agtgagcgag caggttaagt tacatggtat tagtgaagcc acagatgtaa    60
taccatgtaa cttaacctgc ctgcctactg cctcgga                             97

<210> SEQ ID NO 3
<211> LENGTH: 97
<212> TYPE: DNA
<213> ORGANISM: Artificial Sequence
<220> FEATURE:
<223> OTHER INFORMATION: snRNA sequence

<400> SEQUENCE: 3
tgctgttgac agtgagcgaa aagatgaaac gagtgttgaa tagtgaagcc acagatgtat    60
tcaacactcg tttcatcttt ctgcctactg cctcgga                             97

<210> SEQ ID NO 4
<211> LENGTH: 22
<212> TYPE: DNA
<213> ORGANISM: Artificial Sequence
<220> FEATURE:
<223> OTHER INFORMATION: Primer sequence

<400> SEQUENCE: 4
atgtcctttc ggatctcctg cc                                             22

<210> SEQ ID NO 5
<211> LENGTH: 28
<212> TYPE: DNA
<213> ORGANISM: Artificial Sequence
<220> FEATURE:
<223> OTHER INFORMATION: Primer sequence

<400> SEQUENCE: 5
ggtaaacaga gcgctactcc tgtgtgtt                                       28

<210> SEQ ID NO 6
<211> LENGTH: 21
<212> TYPE: DNA
<213> ORGANISM: Artificial Sequence
<220> FEATURE:
<223> OTHER INFORMATION: Primer sequence
```

<400> SEQUENCE: 6
cgccgctaga ggtgaaattc t                                                  21

<210> SEQ ID NO 7
<211> LENGTH: 21
<212> TYPE: DNA
<213> ORGANISM: Artificial Sequence
<220> FEATURE:
<223> OTHER INFORMATION: Primer sequence

<400> SEQUENCE: 7
cgaacctccg actttcgttc t                                                  21

<210> SEQ ID NO 8
<211> LENGTH: 19
<212> TYPE: DNA
<213> ORGANISM: Artificial Sequence
<220> FEATURE:
<223> OTHER INFORMATION: Primer sequence

<400> SEQUENCE: 8
gcagagaagc aaggctcgc                                                     19

<210> SEQ ID NO 9
<211> LENGTH: 19
<212> TYPE: DNA
<213> ORGANISM: Artificial Sequence
<220> FEATURE:
<223> OTHER INFORMATION: Primer sequence

<400> SEQUENCE: 9
cagttgacac actcccggc                                                     19

<210> SEQ ID NO 10
<211> LENGTH: 22
<212> TYPE: DNA
<213> ORGANISM: Artificial Sequence
<220> FEATURE:
<223> OTHER INFORMATION: Primer sequence

<400> SEQUENCE: 10
caagagaagc atccctccag aa                                                 22

<210> SEQ ID NO 11
<211> LENGTH: 23
<212> TYPE: DNA
<213> ORGANISM: Artificial Sequence
<220> FEATURE:
<223> OTHER INFORMATION: Primer sequence

<400> SEQUENCE: 11
tgtttttatt ttcacgccgt ttg                                                23

<210> SEQ ID NO 12
<211> LENGTH: 23
<212> TYPE: DNA
<213> ORGANISM: Artificial Sequence
<220> FEATURE:
<223> OTHER INFORMATION: Primer sequence

<400> SEQUENCE: 12
gacatctgca gccggtagat aag                                                23

<210> SEQ ID NO 13

```
<211> LENGTH: 27
<212> TYPE: DNA
<213> ORGANISM: Artificial Sequence
<220> FEATURE:
<223> OTHER INFORMATION: Primer sequence

<400> SEQUENCE: 13
cattatttgc agagtggagg gtattag                                           27

<210> SEQ ID NO 14
<211> LENGTH: 20
<212> TYPE: DNA
<213> ORGANISM: Artificial Sequence
<220> FEATURE:
<223> OTHER INFORMATION: Primer sequence

<400> SEQUENCE: 14
gggtagagga cagccggtgt                                                   20

<210> SEQ ID NO 15
<211> LENGTH: 25
<212> TYPE: DNA
<213> ORGANISM: Artificial Sequence
<220> FEATURE:
<223> OTHER INFORMATION: Primer sequence

<400> SEQUENCE: 15
gtacaatgac aaaggttctg tgggt                                             25

<210> SEQ ID NO 16
<211> LENGTH: 24
<212> TYPE: DNA
<213> ORGANISM: Artificial Sequence
<220> FEATURE:
<223> OTHER INFORMATION: Primer sequence

<400> SEQUENCE: 16
gtgatttcct tccagcagtt gtaa                                              24

<210> SEQ ID NO 17
<211> LENGTH: 26
<212> TYPE: DNA
<213> ORGANISM: Artificial Sequence
<220> FEATURE:
<223> OTHER INFORMATION: Primer sequence

<400> SEQUENCE: 17
ctcacgctat tggtctcttt taagtg                                            26

<210> SEQ ID NO 18
<211> LENGTH: 21
<212> TYPE: DNA
<213> ORGANISM: Artificial Sequence
<220> FEATURE:
<223> OTHER INFORMATION: Primer sequence

<400> SEQUENCE: 18
cttgctgctg gctctgagaa c                                                 21

<210> SEQ ID NO 19
<211> LENGTH: 27
<212> TYPE: DNA
<213> ORGANISM: Artificial Sequence
<220> FEATURE:
<223> OTHER INFORMATION: Primer sequence

<400> SEQUENCE: 19
```
agtccagggt cttttaagga taaattc                                      27

<210> SEQ ID NO 20
<211> LENGTH: 24
<212> TYPE: DNA
<213> ORGANISM: Artificial Sequence
<220> FEATURE:
<223> OTHER INFORMATION: Primer sequence

<400> SEQUENCE: 20
aaccttcaaa tgcagacact tcac                                         24

<210> SEQ ID NO 21
<211> LENGTH: 20
<212> TYPE: DNA
<213> ORGANISM: Artificial Sequence
<220> FEATURE:
<223> OTHER INFORMATION: Primer sequence

<400> SEQUENCE: 21
gaatccgcca gaacgaagac                                              20

<210> SEQ ID NO 22
<211> LENGTH: 23
<212> TYPE: DNA
<213> ORGANISM: Artificial Sequence
<220> FEATURE:
<223> OTHER INFORMATION: Primer sequence

<400> SEQUENCE: 22
gacatctgca gccggtagat aag                                          23

<210> SEQ ID NO 23
<211> LENGTH: 27
<212> TYPE: DNA
<213> ORGANISM: Artificial Sequence
<220> FEATURE:
<223> OTHER INFORMATION: Primer sequence

<400> SEQUENCE: 23
cattatttgc agagtggagg gtattag                                      27

<210> SEQ ID NO 24
<211> LENGTH: 20
<212> TYPE: DNA
<213> ORGANISM: Artificial Sequence
<220> FEATURE:
<223> OTHER INFORMATION: Primer sequence

<400> SEQUENCE: 24
gccgagggag ttcagtgcta                                              20

<210> SEQ ID NO 25
<211> LENGTH: 23
<212> TYPE: DNA
<213> ORGANISM: Artificial Sequence
<220> FEATURE:
<223> OTHER INFORMATION: Primer sequence

<400> SEQUENCE: 25
agcgctactc ctgtgtgttc ttc                                          23

<210> SEQ ID NO 26
<211> LENGTH: 22
<212> TYPE: DNA

```
<213> ORGANISM: Artificial Sequence
<220> FEATURE:
<223> OTHER INFORMATION: Primer sequence

<400> SEQUENCE: 26
tcctggcgac tcctagatcc ta                                              22

<210> SEQ ID NO 27
<211> LENGTH: 21
<212> TYPE: DNA
<213> ORGANISM: Artificial Sequence
<220> FEATURE:
<223> OTHER INFORMATION: Primer sequence

<400> SEQUENCE: 27
gaaagccctg aggaagttgg a                                               21

<210> SEQ ID NO 28
<211> LENGTH: 22
<212> TYPE: DNA
<213> ORGANISM: Artificial Sequence
<220> FEATURE:
<223> OTHER INFORMATION: Primer sequence

<400> SEQUENCE: 28
tcagcattgc ttcttatcag cc                                              22

<210> SEQ ID NO 29
<211> LENGTH: 18
<212> TYPE: DNA
<213> ORGANISM: Artificial Sequence
<220> FEATURE:
<223> OTHER INFORMATION: Primer sequence

<400> SEQUENCE: 29
cgcagaggcc agaggatg                                                   18

<210> SEQ ID NO 30
<211> LENGTH: 20
<212> TYPE: DNA
<213> ORGANISM: Artificial Sequence
<220> FEATURE:
<223> OTHER INFORMATION: Primer sequence

<400> SEQUENCE: 30
gcacacagga cctgactcca                                                 20

<210> SEQ ID NO 31
<211> LENGTH: 20
<212> TYPE: DNA
<213> ORGANISM: Artificial Sequence
<220> FEATURE:
<223> OTHER INFORMATION: Primer sequence

<400> SEQUENCE: 31
gttctgagat gcggttgctg                                                 20

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32
acctccgaca tgccaactct                                                 20
```

<210> SEQ ID NO 33
<211> LENGTH: 21
<212> TYPE: DNA
<213> ORGANISM: Artificial Sequence
<220> FEATURE:
<223> OTHER INFORMATION: Primer sequence

<400> SEQUENCE: 33
ccgaatcaca aaccacagct t                                           21

<210> SEQ ID NO 34
<211> LENGTH: 22
<212> TYPE: DNA
<213> ORGANISM: Artificial Sequence
<220> FEATURE:
<223> OTHER INFORMATION: Primer sequence

<400> SEQUENCE: 34
agcaatggcc tcacgagttc ta                                          22

<210> SEQ ID NO 35
<211> LENGTH: 21
<212> TYPE: DNA
<213> ORGANISM: Artificial Sequence
<220> FEATURE:
<223> OTHER INFORMATION: Primer sequence

<400> SEQUENCE: 35
ccaggaaaag tttggcagga t                                           21

<210> SEQ ID NO 36
<211> LENGTH: 20
<212> TYPE: DNA
<213> ORGANISM: Artificial Sequence
<220> FEATURE:
<223> OTHER INFORMATION: Primer sequence

<400> SEQUENCE: 36
aagcgcagac caagccatag                                             20

<210> SEQ ID NO 37
<211> LENGTH: 17
<212> TYPE: DNA
<213> ORGANISM: Artificial Sequence
<220> FEATURE:
<223> OTHER INFORMATION: Primer sequence

<400> SEQUENCE: 37
agcgctcacg gctgttg                                                17

<210> SEQ ID NO 38
<211> LENGTH: 20
<212> TYPE: DNA
<213> ORGANISM: Artificial Sequence
<220> FEATURE:
<223> OTHER INFORMATION: Primer sequence

<400> SEQUENCE: 38
cgaagaccct gagaaggaaa                                             20

<210> SEQ ID NO 39
<211> LENGTH: 20
<212> TYPE: DNA
<213> ORGANISM: Artificial Sequence
<220> FEATURE:

```
<223> OTHER INFORMATION: Primer sequence

<400> SEQUENCE: 39
gctgcaagtg tggttctgtg                                               20

<210> SEQ ID NO 40
<211> LENGTH: 18
<212> TYPE: DNA
<213> ORGANISM: Artificial Sequence
<220> FEATURE:
<223> OTHER INFORMATION: Primer sequence

<400> SEQUENCE: 40
tcactggcgc tgcaacaa                                                 18

<210> SEQ ID NO 41
<211> LENGTH: 23
<212> TYPE: DNA
<213> ORGANISM: Artificial Sequence
<220> FEATURE:
<223> OTHER INFORMATION: Primer sequence

<400> SEQUENCE: 41
tctgccgagt agttttcatc gtt                                           23

<210> SEQ ID NO 42
<211> LENGTH: 20
<212> TYPE: DNA
<213> ORGANISM: Artificial Sequence
<220> FEATURE:
<223> OTHER INFORMATION: Primer sequence

<400> SEQUENCE: 42
gaggccctcc ccatatgaga                                               20

<210> SEQ ID NO 43
<211> LENGTH: 18
<212> TYPE: DNA
<213> ORGANISM: Artificial Sequence
<220> FEATURE:
<223> OTHER INFORMATION: Primer sequence

<400> SEQUENCE: 43
gcgccgcact actttggt                                                 18

<210> SEQ ID NO 44
<211> LENGTH: 18
<212> TYPE: DNA
<213> ORGANISM: Artificial Sequence
<220> FEATURE:
<223> OTHER INFORMATION: Primer sequence

<400> SEQUENCE: 44
ggcagcgatg gagaaagc                                                 18

<210> SEQ ID NO 45
<211> LENGTH: 19
<212> TYPE: DNA
<213> ORGANISM: Artificial Sequence
<220> FEATURE:
<223> OTHER INFORMATION: Primer sequence

<400> SEQUENCE: 45
ggacatggtg tgcggagaa                                                19
```